(12) United States Patent
Ben Dor et al.

(10) Patent No.: US 8,060,189 B2
(45) Date of Patent: Nov. 15, 2011

(54) SYSTEM AND METHOD FOR DETECTION OF HEMATOMA

(75) Inventors: Baruch Ben Dor, Bryn Mawr, PA (US); Britton Chance, Marathon, FL (US)

(73) Assignee: Infrascan, inc., Philadelphia, PA (US)

( * ) Notice: Subject to any disclaimer, the term of this patent is extended or adjusted under 35 U.S.C. 154(b) by 561 days.

(21) Appl. No.: 11/919,851

(22) PCT Filed: May 5, 2006

(86) PCT No.: PCT/US2006/017372
§ 371 (c)(1),
(2), (4) Date: Feb. 2, 2009

(87) PCT Pub. No.: WO2006/121833
PCT Pub. Date: Nov. 16, 2006

(65) Prior Publication Data
US 2009/0221919 A1    Sep. 3, 2009

Related U.S. Application Data

(60) Provisional application No. 60/678,519, filed on May 6, 2005, provisional application No. 60/787,383, filed on Mar. 30, 2006.

(51) Int. Cl.
*A61B 5/1455* (2006.01)
(52) U.S. Cl. ........................................ 600/476; 600/473
(58) Field of Classification Search .................. 600/310, 600/407, 473, 475–477
See application file for complete search history.

(56) References Cited

U.S. PATENT DOCUMENTS

| | | |
|---|---|---|
| 5,167,230 A | 12/1992 | Chance |
| 5,402,778 A | 4/1995 | Chance |
| 5,596,987 A | 1/1997 | Chance |
| 5,779,631 A | 7/1998 | Chance |
| 5,873,821 A | 2/1999 | Chance et al. |
| 5,954,053 A | 9/1999 | Chance et al. |
| 5,987,351 A | 11/1999 | Chance |
| 6,134,460 A | 10/2000 | Chance |
| 6,526,309 B1 | 2/2003 | Chance |
| 6,618,614 B1 | 9/2003 | Chance et al. |
| 2005/0113656 A1 | 5/2005 | Chance |
| 2006/0211944 A1 | 9/2006 | Mauge et al. |
| 2006/0211945 A1 | 9/2006 | Mauge et al. |
| 2006/0211946 A1 | 9/2006 | Mauge et al. |
| 2007/0118038 A1 | 5/2007 | Bodecker et al. |

(Continued)

FOREIGN PATENT DOCUMENTS

CA          2103166          11/1992

(Continued)

OTHER PUBLICATIONS

Office of the Secretary of Defense (OSD), Deputy Director of Defense Research & Engineering, Deputy Under Secretary of Defense (Science & Technology), Small Business Innovation Research (SBIR), FY2004.1 Program Description, OSD-1-OSD-13.

(Continued)

*Primary Examiner* — Parikha Mehta
(74) *Attorney, Agent, or Firm* — Morgan Lewis & Bockius LLP

(57) ABSTRACT

A system and method for determining brain hematoma including a handheld device for emitting and detecting radiation with a removable light guide assembly. A method for determining a brain hematoma condition that includes determining optical density of various regions of the brain using near infrared spectroscopy.

15 Claims, 33 Drawing Sheets

U.S. PATENT DOCUMENTS

2007/0118039 A1  5/2007  Bodecker et al.

FOREIGN PATENT DOCUMENTS

| | | |
|---|---|---|
| CA | 1331483 | 8/1994 |
| CA | 2209240 | 7/1996 |
| CA | 2239552 | 6/1997 |
| CN | 96191290 | 1/1998 |
| CN | 96198766 | 2/1999 |
| DE | 68928348 T | 4/1998 |
| DE | 69627477 T | 3/2004 |
| EP | 0441791 | 8/1991 |
| EP | 0591289 | 4/1994 |
| EP | 0808124 | 11/1997 |
| EP | 0906052 | 4/1999 |
| WO | WO0135815 | 5/2001 |

OTHER PUBLICATIONS

The Department of Defense, Small Business Innovation Research (SBIR) Program, Program Solicitation FY04.1.

This Year's 'Eight Great' Business Plans: You Pick the Winner; Knowledge@Wharton; http://knowledge.wharton.upenn.edu/index.cfm?fa=printArticle&ID=980; May 7, 2004; pp. 1-4.

Wharton Entrepreneurial Programs; Wharton Business Plan Competition, Venture Fair, 2003-2004, Final Round Presentations and Award Ceremonies, Monday, Apr. 26, 2004.

Cost Effective, Mobile Medical Imaging System for Detecting Brain Hematomas, Wharton Business Plan Competition Apr. 26, 2004, pp. 1-19.

Portable Near Infrared Technology for Detection of Traumatic Brain Injuries in Operational Environments, Topic No. OSD04-DH4 NIM Inc. Proposal No. O041-DH4-3009, pp. 3-23.

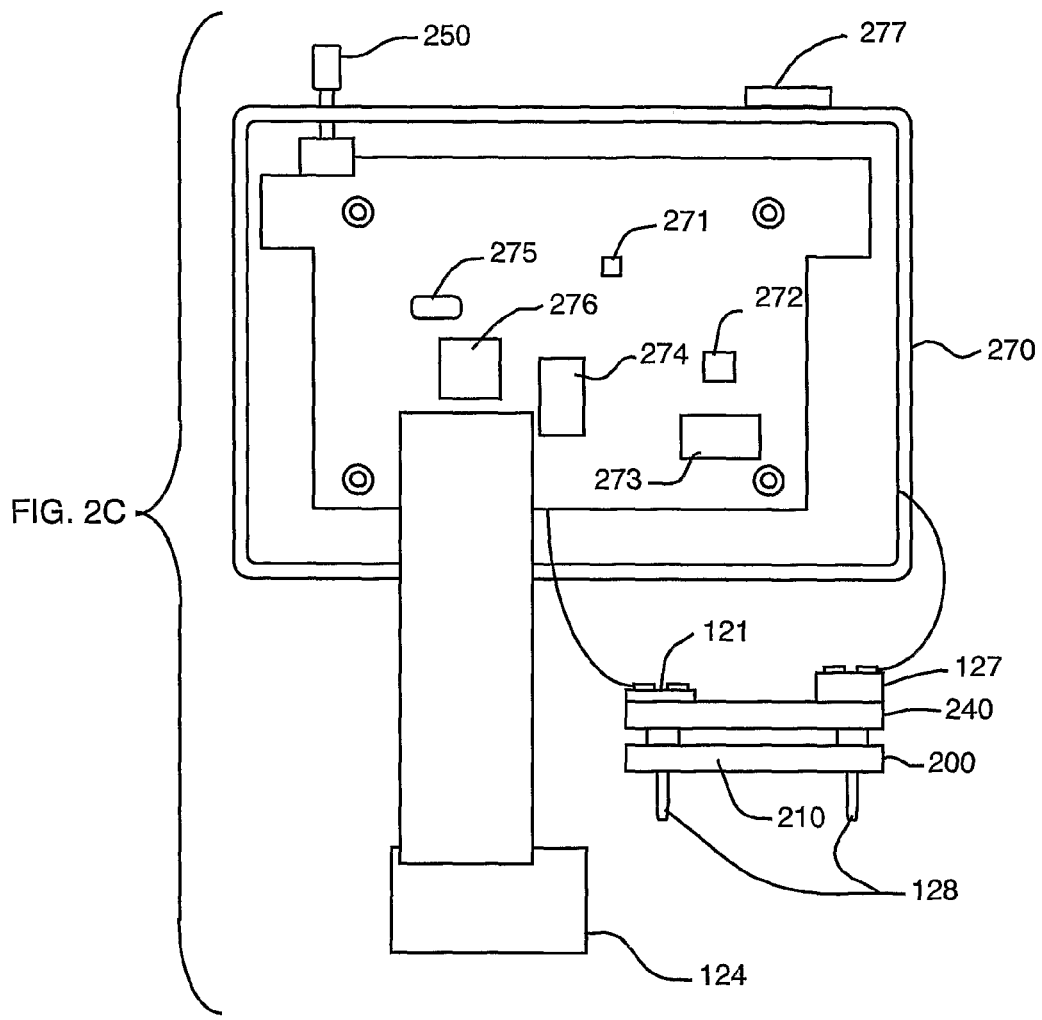

| LASER POWER | VALUE |
|---|---|
| 5 | 2.3 |
| 10 | 9.1 |
| 20 | 19.6 |
| 30 | 30.4 |
| 40 | 39.5 |
| 50 | 51.4 |
| 55 | 55.3 |
| ... | ... |
| 100 | 100 |

1104 →

| GAIN | VALUE |
|---|---|
| 1 | 1.3 |
| 10 | 9.1 |
| 20 | 19.6 |
| 30 | 30.4 |
| 40 | 39.5 |
| 50 | 51.4 |
| 60 | 59.3 |
| ... | ... |
| 100 | 100 |

| COMMAND LABEL | DECIMAL VALUE | BINARY VALUE | BODY LENGTH | BODY BYTE LABELS |
|---|---|---|---|---|
| DO MEASUREMENT | 21 | 00010101 | 6 | BYTE 1: LASER POWER (0-100)<br><br>BYTE 2: NUMBER OF PULSES (0-100)<br><br>BYTE 3: PERIOD OF LASER PULSES (100/10-1000/10)<br><br>BYTE 4: PULSE WIDTH (1-10)<br><br>BYTE 5: GAIN (0-255)<br><br>BYTE 6: AVERAGE 0-NO, 1-YES |

FIG. 13

SYSTEM AND METHOD FOR DETECTION OF HEMATOMA

CROSS-REFERENCE TO RELATED APPLICATIONS

This application is a National Stage of International Application No. PCT/US2006/017372, filed May 5, 2006, which claims the benefit of and priority to U.S. Provisional Application No. 60/678,519, filed May 6, 2005 and U.S. Provisional Application No. 60/787,383, filed Mar. 30, 2006, all of which are hereby incorporated by reference in their entireties.

BACKGROUND

One of the most important principles for the initial resuscitation of a head trauma patient is to promptly identify and surgically evacuate traumatic intracranial hematomas. Hematoma is a condition by which blood accumulates outside blood vessel generally as a result of a hemorrhage or trauma. Unilateral hematoma exists when blood accumulation takes place in one side of the head. Bilateral hematoma exists when blood accumulation exists in both sides of the head.

Time is crucial as the expanding mass lesion can cause death from brainstem compression or cause global ischemic injury. At least one study has shown that a delay of more than 4 hours between injury and the evacuation of a subdural hematoma increased mortality and worsened outcome in survivors.

CT scanning is one means for identifying and localizing localization traumatic intracranial hematomas. Achieving evacuation of intracranial hematomas in 4 hours generally requires an organized system of regional trauma centers, where a patient is initially taken to a nearby trauma center capable of complete treatment of their injury. For those patients with neurological injuries, a CT scan, followed by surgery if necessary, is obtained immediately after the patient is hemodynamically stabilized. However, in emergencies involving trauma to the head in rural areas of the US, in underdeveloped areas of the world and, critically, in the battlefield, timely identification of patients that require surgery can be more difficult.

Moreover, comprehensive trauma centers with 24 hr/day CT scanning are not always immediately available. The primary method for identification of patients with hematomas in these settings is the neurological exam. However, the neurological examination is a poor substitute for CT scan because no single physical sign reliably indicates the presence of a hematoma. Focal neurological findings are found in only a fraction of patients with surgical hematomas. Coma has been reported to occur without the occurrence of a surgical hematoma in 56% of patients with severe head injury. Although patients with intracranial hematomas have increased intracranial pressure (ICP), papilledema is uncommon after head injury, occurring in only 3.5% in one study. A unilateral dilated pupil is commonly identified as one lateralizing sign when it occurs in a patient with a hematoma, but the presence of such a finding does not clearly identify the presence of a surgical hematoma since it is also found in a significant number of patients with diffuse brain injuries.

There is a need, therefore, for a non-invasive system that is capable of detecting intracranial hematoma in-situ following a traumatic brain injury. Such a system is needed that will allow the maximum possible comfort to patient and ease of use for the operator, while maximizing hematoma detection rate and minimizing false alarm rate. Even if the type of hematomas cannot be determined with certainty, the presence of any type of hematoma is the only information required in the field to triage a patient immediately to a hospital with neurosurgical diagnostic and operative capabilities.

It is known that an accumulation of extravascular blood absorbs more near infrared (NIR) light than the intravascular blood. This is attributable to a greater concentration of hemoglobin in the extravascular blood than in blood contained within vessels. Extravascular blood may also have a higher degree of oxygenation than intravascular blood. At certain wavelengths, blood with a higher degree of oxygenation absorbs a different quantity of NIR than blood with a lower degree of oxygenation. U.S. Pat. No. 5,954,053 entitled Detection of Brain Hematoma, which is hereby incorporated by reference as if set forth in its entirety herein, describes systems and methods for detection of brain hematoma based upon concentrations of blood in tissue.

SUMMARY

One embodiment of the present invention exploits these and other phenomena by providing a system and method for detection of hematoma based upon the difference in absorbance of NIR light for intravascular and extravascular blood.

In one embodiment, there is a method of indicating a bilateral hematoma condition including determining an optical density associated with a plurality of brain locations on a right side of a patient's head; determining a first optical density difference between two of the plurality of brain locations on the right side of the patient's head; determining an optical density associated with a plurality brain locations on a left side of the patient's head; determining a second optical density difference between two of the plurality of brain locations on the left side of the patient's head; indicating bilateral hematoma based upon a comparison of the first optical density difference and the second optical density difference to a predetermined optical density difference range.

In one embodiment, there is a method of indicating hematoma that includes determining an optical density difference for at least one pair of contralateral head locations; comparing said optical density differences to a predetermined range of optical density differences; and diagnosing a hematoma condition in each of the contralateral head locations based upon the relationship between the optical density differences and the predetermined range of optical density differences.

In one embodiment, there is a method of indicating a bilateral hematoma condition that includes determining an optical density associated with each of a patient's frontal lobes, temporal lobes, occipital lobes and parietal lobes; for each side of the patient's head determining a frontal/temporal optical density difference a frontal/parietal optical density difference, a frontal/occipital optical density difference, a temporal/parietal optical density difference, a temporal occipital optical density difference, and a parietal/occipital optical density difference; indicating bilateral hematoma for at least one of the patient's frontal, temporal, occipital and parietal lobe pairs based upon a comparison between a predetermined frontal/temporal optical density difference range to the frontal/temporal optical density differences, a predetermined frontal/parietal optical density difference range to the frontal/parietal optical density differences, a predetermined frontal/occipital optical density difference range to the frontal/occipital optical density difference, a predetermined temporal/parietal optical density difference range to the temporal/parietal optical density difference, and a predetermined temporal/occipital optical density difference range to the temporal/occipital optical density difference.

In one embodiment of the method, determining an optical density is performed by a system comprising a hand held detection device having a base with at least one radiation detector, at least one light source and a removable light guide assembly having at least one detector light guide configured to align with the radiation detector and at least one source light guide configured to align with the light source, the light guide assembly being removably secured to the base.

In one embodiment, there is a system for detection of hematoma that includes a handheld probe having a source of infrared light, a detector of infrared light; and a light guide assembly including a base, a source light guide that transmits infrared light from the source to a tissue region, and a detector light guide that transmits at least a portion of the infrared light passing through the tissue region to the detector, wherein the source light guide and the detector light guide are each secured to the base; a processor linked to the probe, configured to provide instructions to the probe and configured to process data transmitted by the probe, the processor having a display for indicating the presence of hematoma based upon a characteristic of the infrared light passing through the tissue. In one embodiment of the system, the characteristic of the infrared light passing through the tissue is an optical density associated with a region of the brain.

In one embodiment of the system, the probe and processor are housed in a common housing. In other embodiments of the system, the probe and the processor are linked with a wireless link or a wired link. In still another embodiment of the system, the base is contiguous with the source light guide and the detector light guide, the light guide assembly being readily removable and replaceable. In yet another embodiment of the system, the light guide assembly is readily removable and replaceable. In a further embodiment of the system, the light guide assembly is configured to be removed and replaced between patients. In another embodiment of the system, the light guide assembly is configured to be removed without tools. In a further embodiment of the system, the light guide assembly is disposable. In one embodiment of the system, the base of the light guide assembly is a molded cover having a contiguous lip, contiguous light guide cladding, a contiguous light dam associated with the light source and a contiguous light dam associated with the detector.

In one embodiment there is a hand held hematoma detection device that includes a base having at least one radiation detector; at least one light source; a removable light guide assembly having at least one detector light guide configured to align with the radiation detector; at least one source light guide configured to align with the light source; the light guide assembly being removably secured to the base.

One embodiment of the device also includes a sealed securement between the base and the removable light guide assembly. In one embodiment of the device, the sealed securement includes a friction fit between the base and the disposable light guide assembly. In another embodiment of the device, the light guide assembly also includes at least one external support. In one embodiment of the device, at least one of the detector light guides and the source light guides are configured to resiliently depress relative to the base. In a further embodiment of the device, at least one of the detector light guide and the source light guide are configured to apply uniform pressure to the surface of a scalp. In a still further embodiment of the device, the detector light guide and the source light guide protrude from a distal end of the light guide assembly and the light guide assembly further includes a lip at the proximal end of the light guide assembly. In one embodiment of the device, the light guide assembly includes a cover having a contiguous lip, contiguous cladding radially disposed about the detector light guide, contiguous cladding radially disposed about the source light guide, a contiguous light dam associated with the light source and a contiguous light dam associated with the detector.

Reference is made to the accompanying drawings in which are shown illustrative embodiments of the invention, from which its novel features and advantages will be apparent.

In the drawings:

FIG. 2C illustrates one embodiment of the probe of the present invention.

FIG. 11 illustrates one embodiment of calibration tables for use in embodiments of the present invention.

FIG. 13 illustrates one embodiment of a command summary of a Do Measurement command of the present invention.

DESCRIPTION OF PREFERRED EMBODIMENTS

Figure 1B:
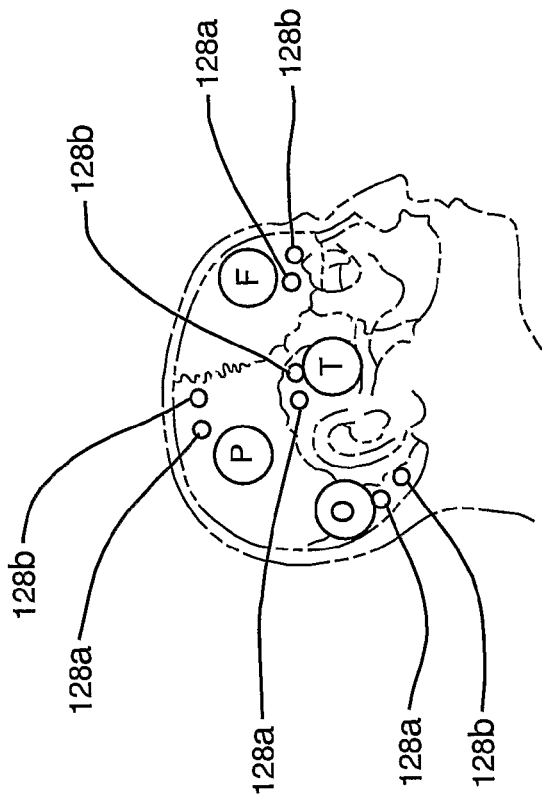
FIGS. 1A and 1B depict the eight tissue regions of brain and one embodiment of probe placement in each of those locations.

Reference will now be made in detail to preferred embodiments of the present invention, examples of which are illustrated in the accompanying drawings. Wherever possible, in certain embodiments, the same reference numbers will be used throughout the drawings to refer to the same or like parts. To provide a thorough understanding of the present invention, numerous specific details of preferred embodiments are set forth including material types, dimensions, and procedures. Practitioners having ordinary skill in the art will understand that the embodiments of the present invention may be practiced without many of these details. In other instances, well-known devices, methods, and processes have not been described in detail to avoid obscuring the invention.

As described in more detail below, in one embodiment of the present invention, near-infrared spectroscopy (NIRS) provides a basis for a practical solution to the problem of early identification of intracranial hematomas in the field. In one embodiment of the present invention, there is disclosed an easy-to-use, miniaturized, portable and battery operated NIRS unit and method for using same.

A principle used in identifying intracranial hematomas with NIRS is that extravascular blood absorbs NIR light more than intravascular blood since there is a greater (usually 10-fold greater) concentration of hemoglobin in the acute hematoma than in the brain tissue where blood is contained within vessels. Therefore, the absorbance of NIR light would be greater (and therefore the reflected light less) in tissue containing a hematoma, than in uninjured tissue.

Under normal conditions, the brain absorbs light symetrically as between the left and right side of the brain (e.g., as between the left temporal and right temporal lobes, the left parietal and right parietal lobes, the left occipital and right occipital lobes and the left frontal and right frontal lobes). In one embodiment of the present invention, the differential in light absorption is predictably different between regions of the brain on the same side of the head (e.g., as between right frontal and right parietal, right frontal and right temporal, right frontal and right occipital etc.). Optical light source(s) or emitter(s) of specified wavelength ranges and photodetector(s) are therefore configured, in one embodiment of the present invention, to allow proper light (e.g., in the near infrared spectrum) absorption measurements in a desired volume of tissue at a desired location. In one embodiment, a proper comparison of the tissue's absorptive properties is then made. That comparison preferably includes a comparison of tissue on opposite sides of a patient's head and/or tissue on the same side of a patient's head.

In one embodiment, described in detail below, an NIRS probe is placed successively in the left and right frontal, temporal, parietal, and occipital areas of the head and the absorbance of light at one or more selected wavelengths is recorded. In another embodiment, an NIRS probe is used to record data regarding the regions of one side of the head (e.g., frontal, temporal, parietal, and occipital) and then on the other side of the head. In one embodiment, a side of patient's head is always scanned in four locations. In one embodiment those four locations include frontal, temporal, parietal and occipital.

In one embodiment both sides of a patient's head are scanned in a total of eight regions of the brain. In one embodiment, illustrated in FIGS. 1A and 1B, the location of eight regions of the brain of relevance to the present invention include: Frontal—left/right forehead, above the frontal sinus; Temporal—in the left/right temporal fossa; parietal—above the left/right ear, midway between the ear and the midline of the skull; and Occipital—behind the left/right ear, midway between the ear and the occipital protuberance.

Figure 1A:
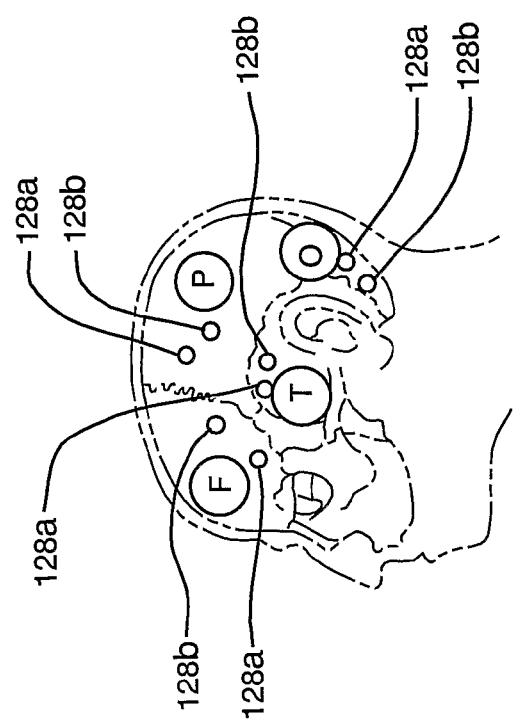
Figure 1C:
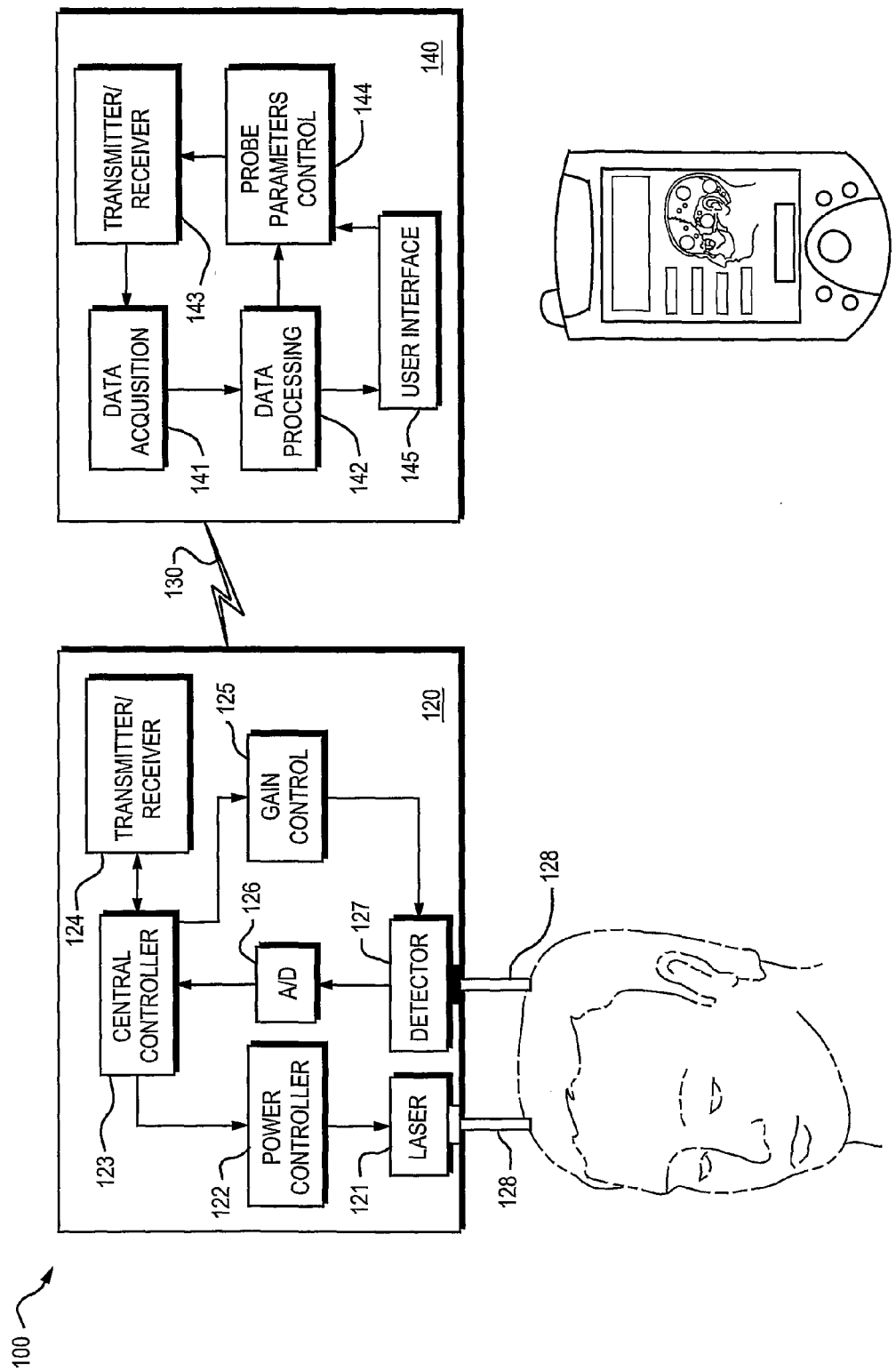
FIG. 1C depicts a system of the present invention.

System 100, FIG. 1C illustrates one embodiment of the present inventive system 100. System 100 includes at least one probe 120 and at least one processor 140.

In one embodiment, each processor 140 controls a plurality of probes 120. In one embodiment, probe 120 includes at least one light source 121 (e.g., at least one laser), power control 122, central controller 123, gain control 125, at least one detector 127, A/D circuit 126, and light guides 128.

In one embodiment, central controller 123 is an 8051 micro-controller of Silicon Laboratories (Part No. C8051F001) having built-in functionality to control system hardware and perform A/D conversion of detector signals as described herein. In an embodiment of the present invention, central controller 123 controls and synchronizes all functions of probe 120. In one embodiment, central controller 123 is configured to control gain settings of detector(s) 127. In one embodiment, central controller 123 is configured to control power settings of light source 121 (e.g., laser power).

In one embodiment, A/D circuit 126 digitizes readings (e.g., detection measurements) of detector(s) 127 for transmission to processor 140.

In one embodiment, power controller 122 preferably controls the power of light source 121. In one embodiment, power controller 122 is an iC-WJB driver from iC-Haus.

Figure 1D:
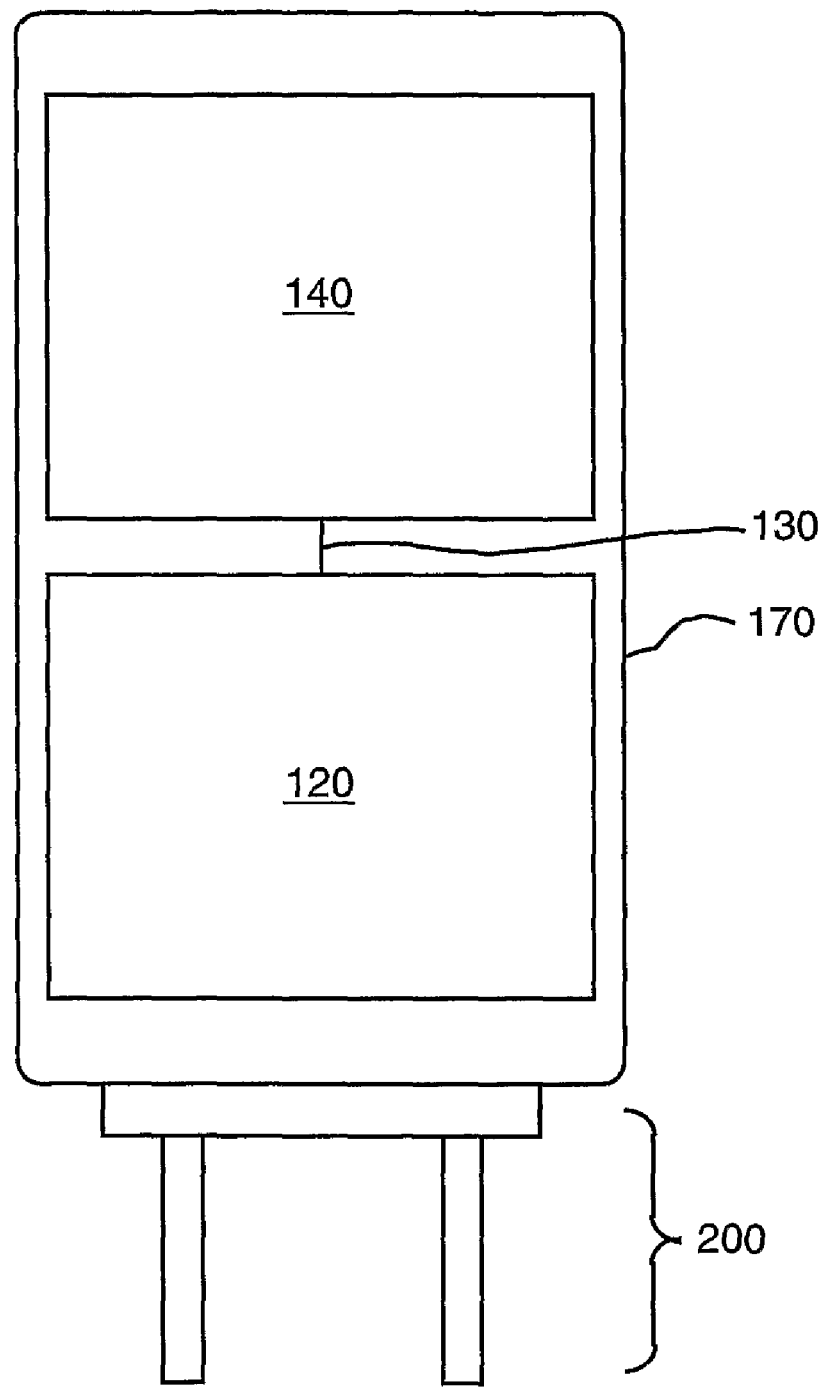
FIG. 1D depicts a system of the present invention.

In one embodiment (e.g., FIG. 1D), probe 120 and processor 140 are contained in a common housing 170. In one embodiment, processor 140 is located within probe 120. In one embodiment, processor 140 and probe 120 are independently housed and are connected by data link 130 (e.g., FIG. 1C). In one embodiment, probe 120 includes transmitter/receiver 124. In one embodiment, transmitter/receiver 124 is configured to transmit and receive data (e.g., digitized detection measurements) from detector 127. In one embodiment, transmitter/receiver 124 is a Bluetooth® transmitter/receiver manufactured by connectBlue (Part No. cB-OEMSPA13I-02). In one embodiment, data link 130 is any data link. In one embodiment, data link 130 preferably is a wireless data link. In one embodiment, data link 130 is a wired data link.

In one embodiment, probe 120 further includes a battery, for example a rechargeable Li-Ion battery (e.g., a 3.3V, 500 mAH battery). In one embodiment, probe 120 permits a minimum of two (2) hours of operation without a charge.

In the embodiment of FIG. 2C, probe 120 includes housing 270. Within housing 270, probe 120 includes a battery charger 271, laser driver 272, memory 273, measure button interface 274, master clock 275, processor 276, and Bluetooth® module 124. Extending from housing 270 is on/off switch 277 and measurement switch 250. In one embodiment, at least one portion of optical bench 240 is contained within housing 270. In one embodiment, an outer portion of optical bench 240 is exposed outside of housing 270. As illustrated in FIG. 2C, light guide assembly 200 is configured to engage optical bench 240.

Processor. In one embodiment, processor 140 is a mobile computing platform such as a laptop computer, handheld computer or any other easily maneuvered processing device. In one embodiment, processor 140 includes a memory. In another embodiment, processor 140 is linked to a remote memory. In one embodiment, processor 140 is an HP iPAQ h4355 Pocket PC. In one embodiment, processor 140 is a simple controller (e.g., a simple controller with limited computing power). In the embodiment illustrated in FIG. 1C, processor 140 includes data acquisition module 141, data processing module 142, probe parameters controller 144 and user interface 145 (e.g., a graphical user interface (GUI)). In a preferred embodiment, processor 140 also includes transmitter/receiver 143. In one embodiment, transmitter/receivers 124, 143 are configured to transmit and receive wireless data (e.g., a Bluetooth® transmitter/receiver). In the embodiment of FIG. 1C, transmitter/receiver 143 and transmitter/receiver 124 are configured to communicate between processor 140 and probe 120 via wireless link 130.

In one embodiment, the protocol for communication between probe 120 and processor 140 describes the initialization of communications, handshaking, command transfer from processor 140 to probe 120, measurement data transfer from probe 120 to processor 140 and termination of communication between processor 140 and probe 120.

In one embodiment, the communications protocol provides communication on a packet basis. In one embodiment the communications protocol for communicating between probe 120 and processor 140 is a packet structure protocol.

Light Source 121. Light source 121 may be any light source that will deliver a desired light spectrum (e.g., NIR spectrum) to detectors 127 via the tissue of interest to achieve the objectives of this invention. In one embodiment, light source 121 emits light in the infrared spectrum, more preferably in the NIR spectrum and even more preferably at a wavelength spectrum of from 730 nm to 860 nm. In one embodiment, the wavelength of light source 121 is selected to correspond to that wavelength which is substantially equally absorbed by oxygenated blood and non-oxygenated blood. In a preferred embodiment, light source 121 transmits light at a wavelength of approximately 805 nm. In one embodiment, the approximately 805 nm wavelength is emitted from an 808 nm wavelength laser which can be more readily available than an 808 nm wavelength laser. In one embodiment, light source 121 is an NIR laser diode. In one embodiment, light source 121 includes a DL-7141-035 diode laser from Sanyo (having up to 100 mV at 808 n nm). In one embodiment, light source 121 is selected for its small size, power consumption, and exit beam geometry. In one embodiment, light source 121 has a parallel narrow focused geometry. In one embodiment light source 121 has a height of between approximately 3 mm and approximately 10 mm. In one embodiment, light source 121 has a diameter of between approximately 3 mm and approximately 10 mm. The power consumption in one embodiment of light source 121 is as little as possible. In a preferred embodiment, light source 121 has a circular exit beam geometry. In one embodiment, light source 121 has an exit beam with a diameter of less than approximately 1.5 mm. In one embodiment, light source 121 has an exit beam diameter of approximately 1 mm.

Figure 2A:
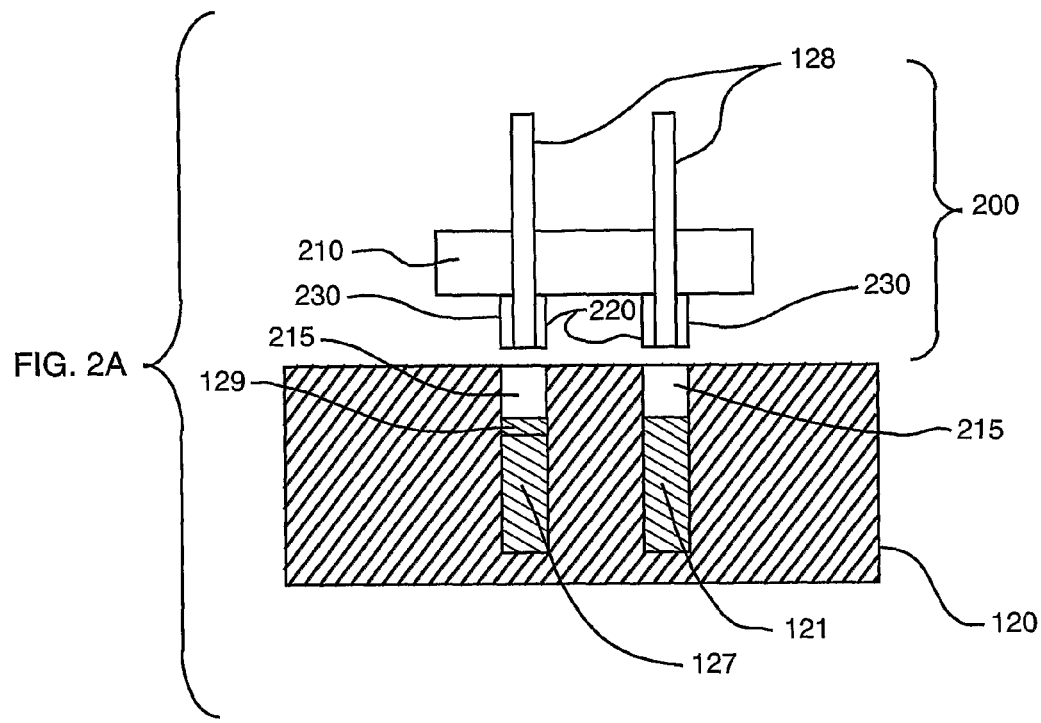
FIGS. 2A-2B depicts two embodiments of probes of the present invention.
Figure 2B:
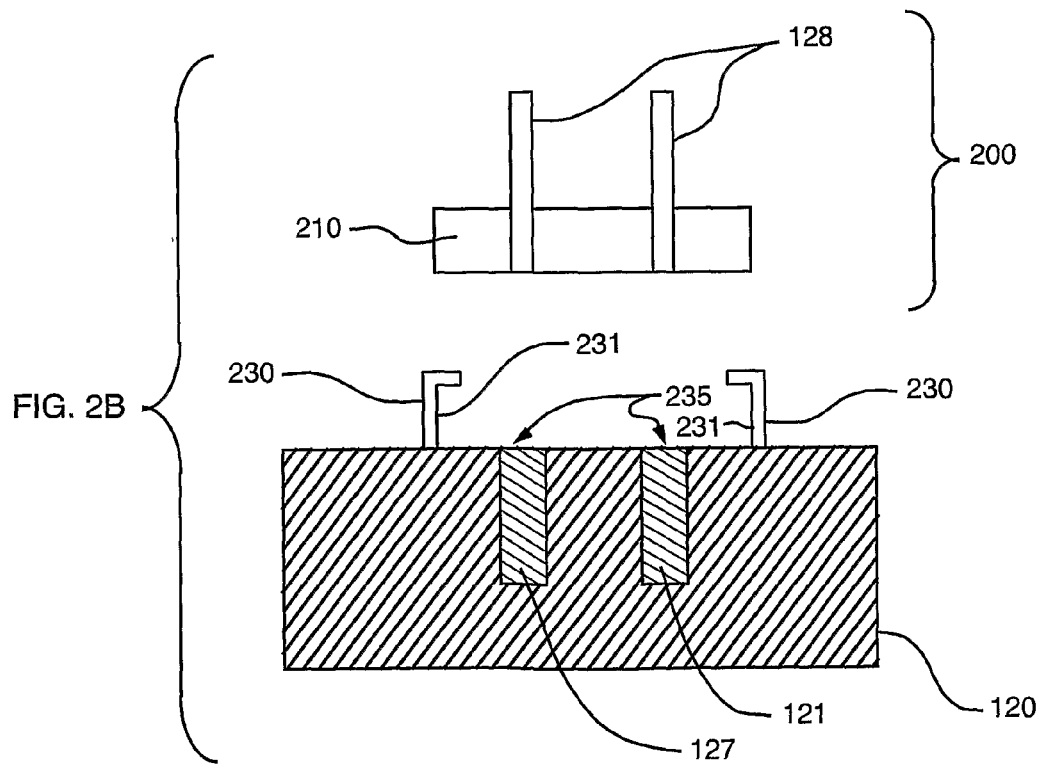
Figure 2D:
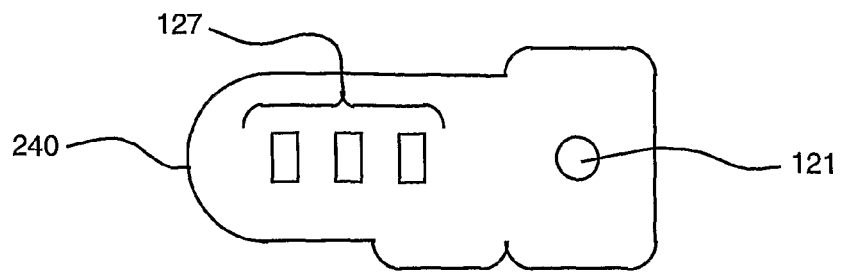
FIG. 2D illustrates one embodiment of an optical bench of the present invention having one light source and three detectors.
Figure 2E:
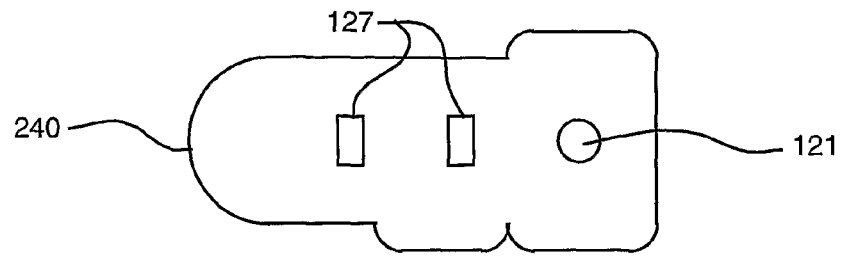
FIG. 2E illustrates one embodiment of an optical bench having one light source and two detectors.
Figure 2F:
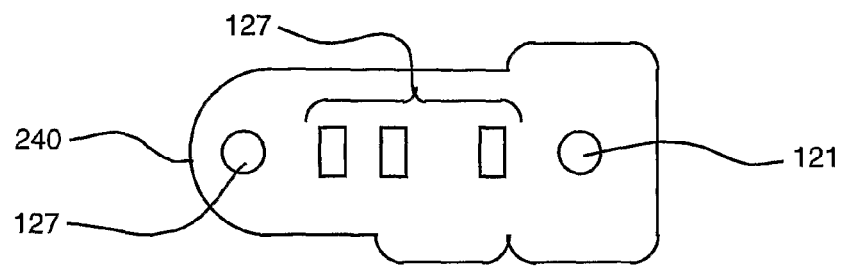
FIG. 2F illustrates one embodiment of an optical bench having two light sources and three detectors.
Figure 2G:
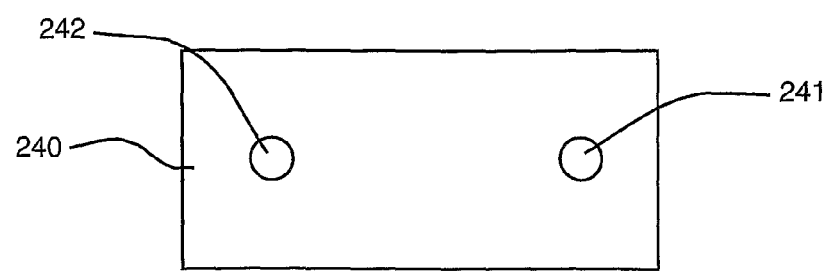
FIG. 2G illustrates one embodiment of an optical bench of the present invention.
Figure 2H:
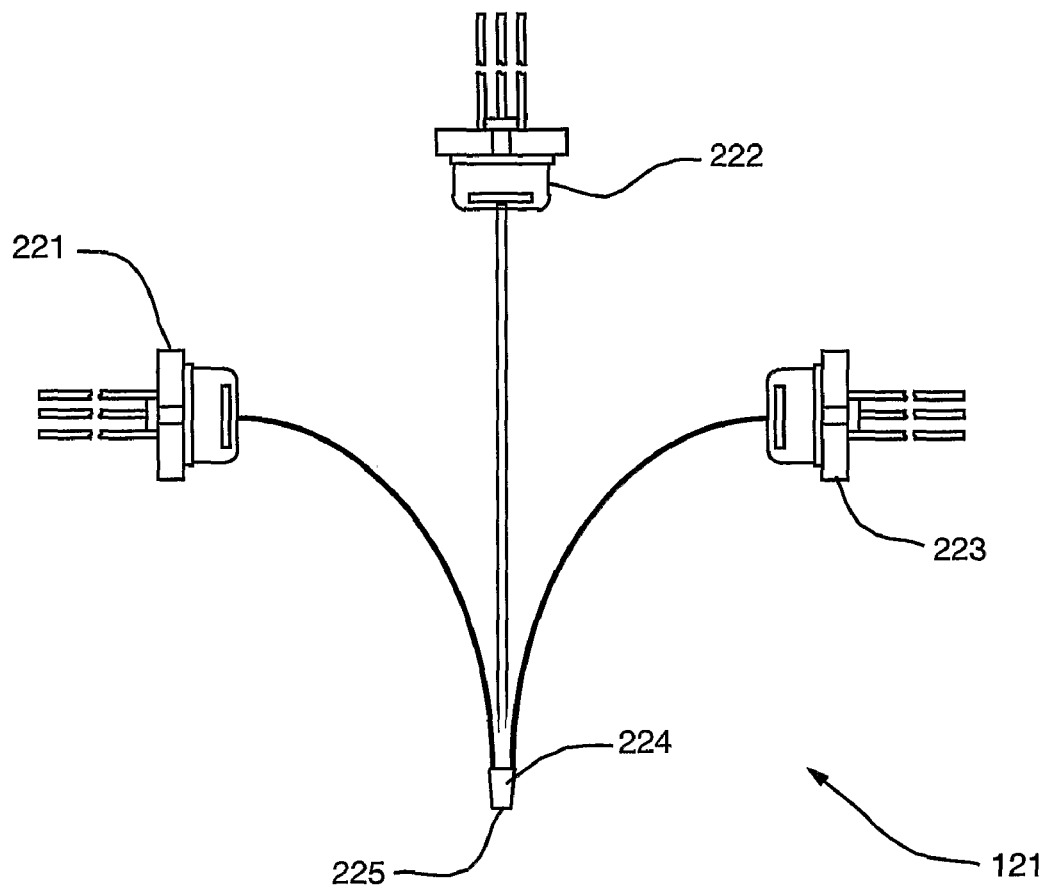
FIG. 2H illustrates one embodiment of a light source of the present invention.

In one embodiment, illustrated in FIG. 2H, light source 121 is a multiple wavelength light source. In one embodiment, light source 121 includes two or more wavelength options. In another embodiment, light source 121 includes three or more wavelengths. In one embodiment light source 121 includes a three wavelength LED. In one embodiment, light source 121 has three selectable wavelengths that are approximately 760 nm, approximately 805 nm, and approximately 850 nm.

In one embodiment of FIG. 2F, light source 121 includes first diode laser 221, second diode laser 222, third diode laser 223 and beam combiner 224. In one embodiment first diode laser 221 is a 760 nm diode laser, second diode laser 222 is an 805 nm diode laser and third diode laser 223 is an 850 nm diode laser. In one embodiment, light propagates from first, second and third diode lasers 221, 222, 223 via fixed light guides or fiber optics through beam combiner 224. In one embodiment exit window 225 is an approximately 1.5 mm diameter exit window. In one embodiment, the signal analysis used is the same or similar to that disclosed in Kurth, C. D., Levy, W. J., and Mccann, J., *Near infrared spectroscopy cerebral oxygen saturation thresholds for hypoxia-ischemia in piglets*, J. Cereb. Blood Flow Metab, 22: 335-341 (2002).

Detector 127. In one embodiment, to minimize background light interference, detector 127 includes band pass filter 129 (illustrated in FIG. 2A) configured for a wavelength that is compatible with the wavelength of light source 121. In one embodiment, detector 127 is Detector Part No. S9269 manufactured by Hamamatsu. In one embodiment, band pass filter 129 separates light outside a wavelength range. In one embodiment, filtered light is outside a range of between approximately 760 nm and approximately 820 nm, more preferably outside a wavelength range of between approximately 800 and approximately 810 nm and even more preferably outside a wavelength range of between approximately 805 and approximately 808 nm.

In one embodiment, two detectors 127 and one light source 121 are included in probe 120 (FIG. 2E). In another embodiment, three detectors 127 and two light sources 121 are included in probe 120 (FIG. 2F). In one embodiment (e.g., FIG. 2D), three detectors 127 are spaced approximately 2 cm, approximately 3 cm and approximately 4 cm respectively from light source 121.

FIG. 1C illustrates an embodiment of the present invention having one light source 121 and one detector 127. In one embodiment, the distance between detectors 127 and light source 121 is fixed. The preferred distance between detectors 127 and light sources 121, in one embodiment, is between approximately 3 cm and approximately 5 cm and is more preferably approximately 4.5 cm. In one embodiment, detector 127 and light source 121 are included in an assembly of optical bench 240. In an embodiment illustrated in FIG. 2D, optical bench 240 includes one detector 127 and three light sources 121. In one embodiment, light source 121 in FIG. 2D is spaced from detectors 127 at 2 cm, 3 cm and 4 cm respectively. In one embodiment, optical bench 240 includes a laser exit window 241 and an infrared filter 242 that covers at least one detector 127 (FIG. 2G).

In one embodiment, multiple detectors are included in probe 120. In one embodiment, the number of detectors is determined by the number of wavelengths included in light source 121. For example, in one embodiment, probe 120 includes a three wavelength light source (or e.g., three light sources each with a different wavelength) and three detectors (e.g., one detector associate with each light source). In one embodiment, each detector is associated with a separate amplification circuit. In one embodiment, separate amplification circuits accommodate varying distances between a light source exit beam and a detector.

Light Guides. Light guides 128 are preferably made of plastic or glass or any other material selected to achieve the objections of the invention. As illustrated in FIGS. 2A and 2B, in one embodiment, detector 127 and light source 121 are configured for operation through light guides 128.

In one embodiment, light guides 128 are fiber optic bundles. In one embodiment, light guides 128 include a rigid fiber optic bundle from Edmund Scientific having a diameter of 1.6 mm and a length of 25.4 mm. In one embodiment, light guides 128 include a single optic fiber. In one embodiment, light guides 128 extend a distance of approximately 5 mm from probe 120 and have a maximum diameter up to approximately 2 mm. In one embodiment, the minimum radius of light guides 128 is approximately 6.5 cm.

In one embodiment light guides 128 are configured to contact flat and curved surfaces (e.g., the varying surfaces of a skull). In one embodiment, the spacing of light guides 128 is configured to accommodate the curved shapes found at different locations on the head. In another embodiment, one or more of light guides 128 are resiliently depressible (described in more detail below) to accommodate different shapes found on a skull.

In one embodiment, the light guides 128 are configured to contact tissue without causing irritation (e.g., pain, scratching or other discomfort). In one embodiment, illustrated in FIG. 3C, light guides 128 include a rounded distal end portion 310 to accommodate contact with a patient's skin without causing discomfort or harm to the patient.

In one embodiment, light guides 128 are in a hairbrush configuration such as that described in U.S. Pat. No. 6,618, 614 which is hereby incorporated by reference as if set forth in its entirety herein. In one embodiment, light guides 128 are preferably configured to avoid trapping a patient's hair between light guide 128 and the patient's scalp. In one embodiment, light guides 128 are configured to accommodate a scalp with significant amount of hair. For example, in one embodiment, the tips of light guides 128 extend approximately 5 mm or more from probe 120 to maintain a gap sufficient to account for hair between the light guide tip and probe 120.

FIGS. 3A-3D illustrate exemplary configurations of light guides 128. In an embodiment illustrated in FIG. 3A, light guide 128 is configured to include a plurality of distal fibers 302 proximate distal end 304 of light guide 128. In one embodiment, light guide 128 includes trunk 305 and distal fibers 302. In one embodiment, the plurality of distal fibers 302 are arranged in a substantially equally or non-equally spaced pattern. In one embodiment, light guide 128 includes between 4 and 10 distal fibers 302. In one embodiment, illustrated in FIG. 3B, light guide 128 includes seven distal fibers 302 arranged in a substantially equally spaced substantially hexagonal pattern.

Figure 4A:
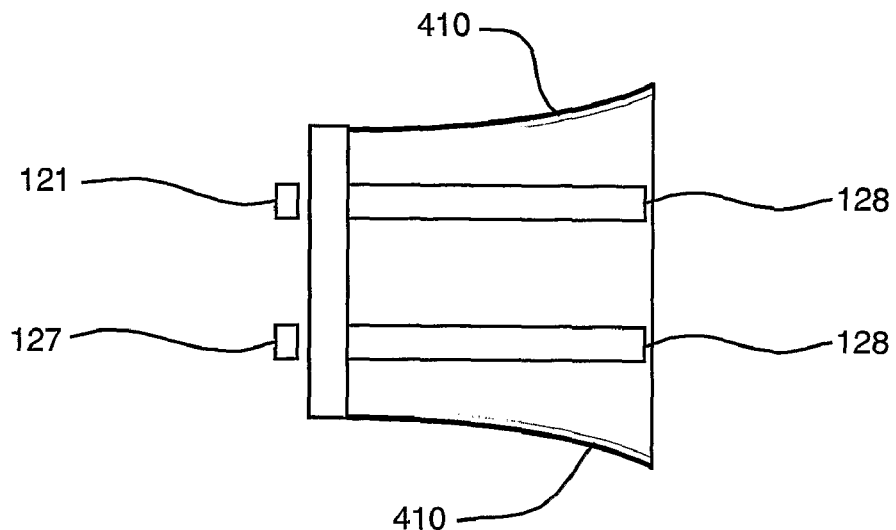
FIGS. 4A and 4B illustrate side sectional elevation of light guide assemblies of the present invention.
Figure 4B:
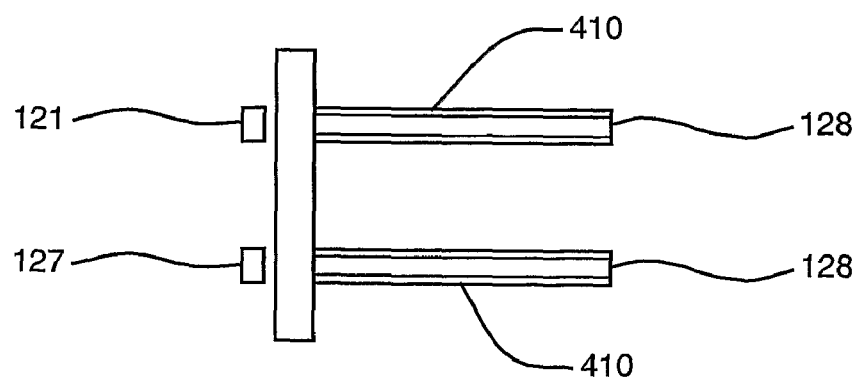

Shadow. In one embodiment, illustrated in FIGS. 4A and 4B, probe 120 includes cover 410 (e.g., a shadow that minimizes background illumination interference) that blocks the transmission of light. In one embodiment, cover 410 is an opaque cover. FIG. 4A illustrates one embodiment in which a single cover 410 covers both a light guide 128 aligned with detector 127 and light guide 128 aligned with light source 121. In the embodiment of FIG. 4B, cover 410 is an opaque covering, radially disposed about each light guide 128.

Light Guide Assembly. In some embodiments, illustrated in FIGS. 2A, 2B, 2C, 14A-14C, 15A, 16A, 16B, 16D, 16E, 16G, 16I and 16J, there is a light guide assembly 200, 1400, 1500, 1600. In one embodiment, light guide assembly 200, 1400, 1500, 1600 includes base 210, 1402, 1502, 1602. In one embodiment, light guides 128, 1428, 1628 are connected to base 210, 1402, 1502, 1602. In one embodiment described in more detail below, light guides do not move relative to base. In other embodiment, also described below, light guides are attached to base 210, 1402, 1502, 1602 such that the light guides move (e.g., in a resiliently depressible way) relative to the base. In one embodiment, light guide assembly 200, 1600 includes a plurality of light guides 128, 1628. In one embodiment, the plurality of light guides is two, three four, five or more light guides.

Figure 3A:
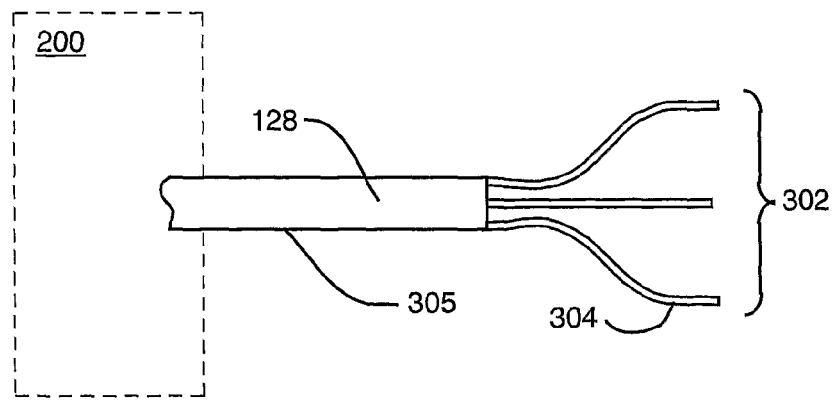
FIGS. 3A-3D illustrate exemplary embodiments of light guides of the present invention.
Figure 3B:
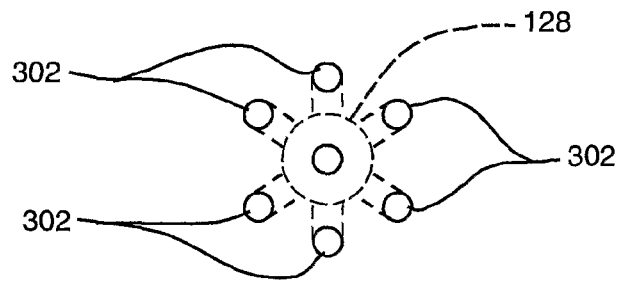
Figure 3C:
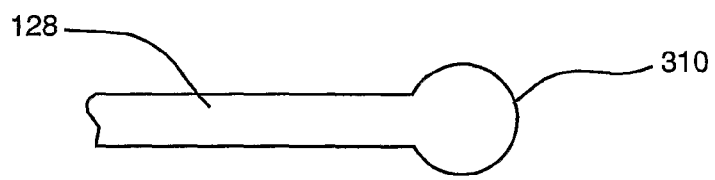
Figure 3D:
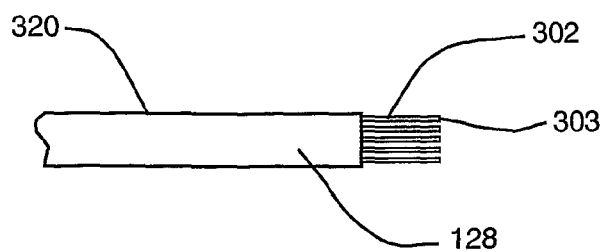

In one embodiment, base 210 is fixed to a cladding 320 surrounding light guides 128 (FIG. 3D). In one embodiment, light guide assembly 200, 1400, 1500, 1600 includes bundled fibers 303 (FIG. 3A). In one embodiment, fibers 302 are removably or non-removably attached (e.g., glued) within light guide assembly 200, 1400, 1500, 1600 to permit easy removal of light guides 128 from probe 120. In another embodiment, base 210 and light guides 128 are contiguous. In one embodiment shown in FIG. 2A, light guide 128 passes through base 210.

Figure 14A:
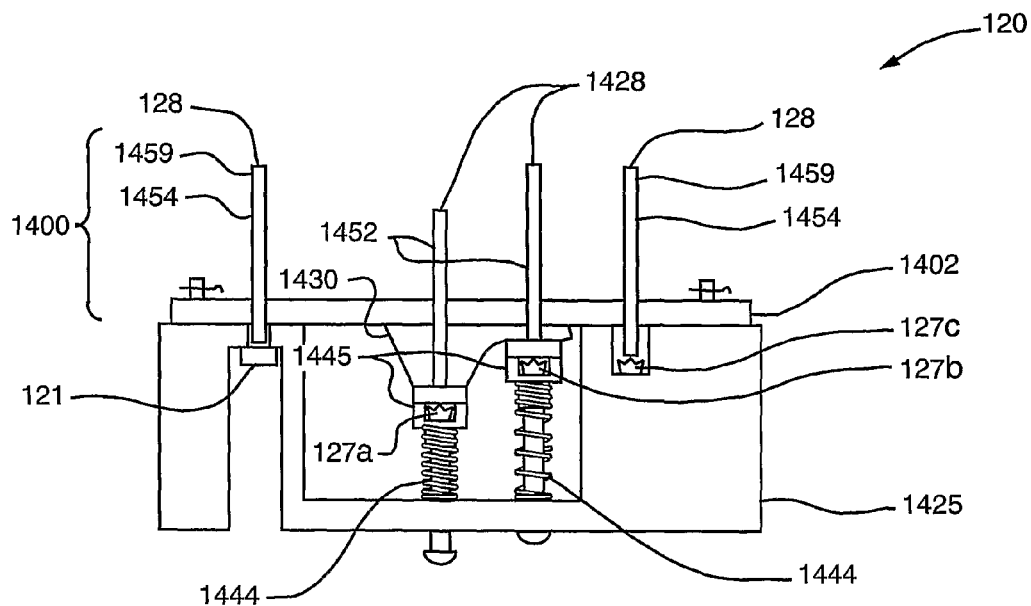
FIG. 14A illustrates one embodiment of the present invention with resiliently depressible light guides.
Figure 14B:
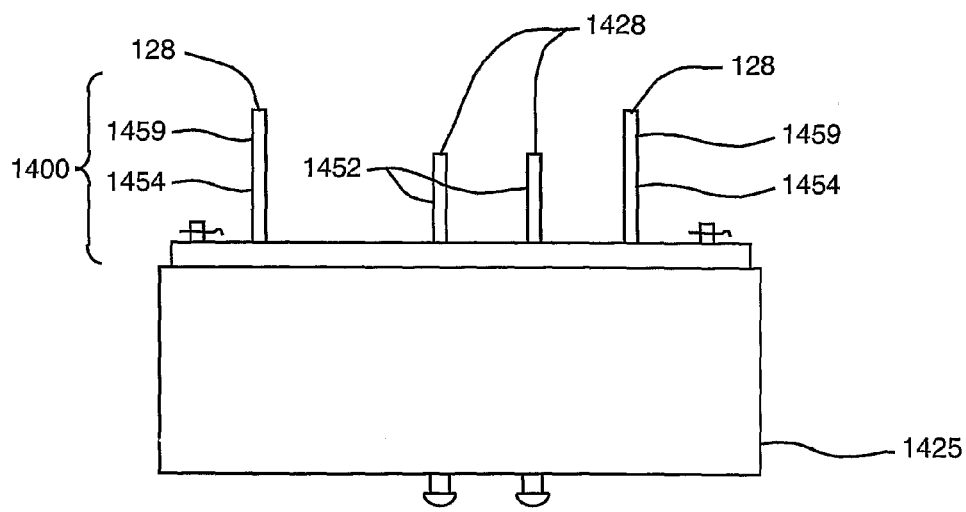
FIG. 14B illustrates a prototype of one embodiment of a probe of the present invention with resiliently depressible light guides.
Figure 14C:
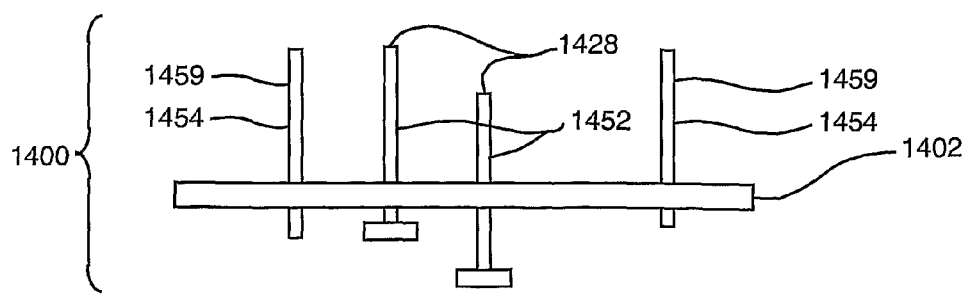
FIG. 14C illustrates a prototype of one embodiment of a portion of a disposable light guide assembly of the present invention.

In one embodiment, light guide assembly 200, 1400, 1500, 1600 is removably secured to probe 210 (e.g., directly to probe 210) or to an optical bench that is secured to probe 210 (e.g., FIG. 14A, 14B, 14C). In one embodiment, light guide assembly 200, 1400, 1500, 1600 is configured to mount into probe 120 such that light guides 128, 1428, 1628 align appropriately with light source 121 and detector 127. In one embodiment, light guides 128, 1428, 1628 preferably substantially abut light source 121. In one embodiment, illustrated for example in FIG. 2C, light guide assembly 200 is configured to make aligned contact with optical bench 240 (including light source 121 and detector 127) when light guide assembly 200 is attached to probe 120 (see FIG. 2C). In one embodiment, light guide assembly 200 is configured such that, for example, light guides 128 can be used in connection with either light source 121 or detector 127. In another embodiment, light guide assembly 200, 1400, 1500, 1600 are configured such that a specific light guide 128, 1428, 1628 is aligned with either a detector 127 or a light source 121.

In one embodiment of light guide assembly 200 (illustrated in FIG. 2A, 2B) light guides 128 protrude below base 210. In one embodiment, collars 220 are radially disposed about light guides 128. In one embodiment, collars 220 are configured to secure light guides 128 within apertures 215 of probe 120 (or for example, within the aperture of an optical bench). In embodiments where light guides 128 are a plurality of bundled fibers, collar 220 preferably includes fiber cladding 320. In a preferred embodiment, the depth and diameter of aperture 215 is configured to secure light guide assembly 200 to probe 120 and to protect light source 121 and detector 127.

Figure 16A:
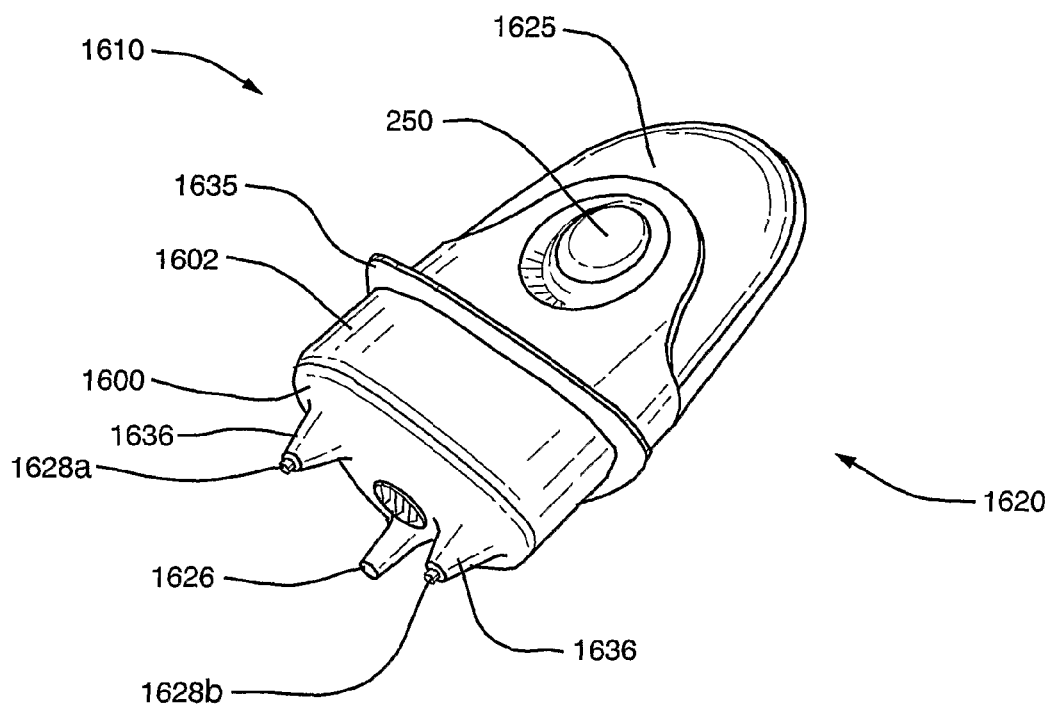
FIG. 16A illustrates a top view of a probe of the present invention.
Figure 16B:
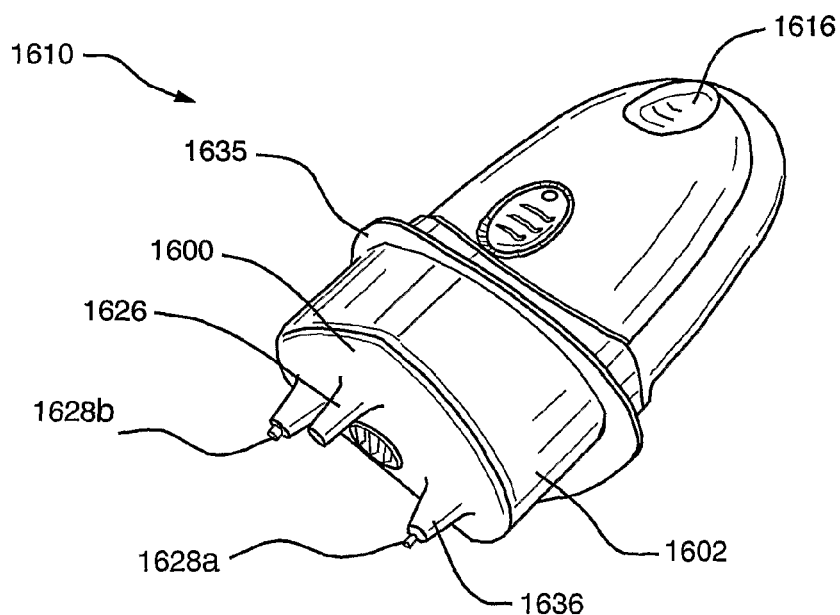
FIG. 16B illustrates a bottom view of a probe of the present invention.
Figure 16C:
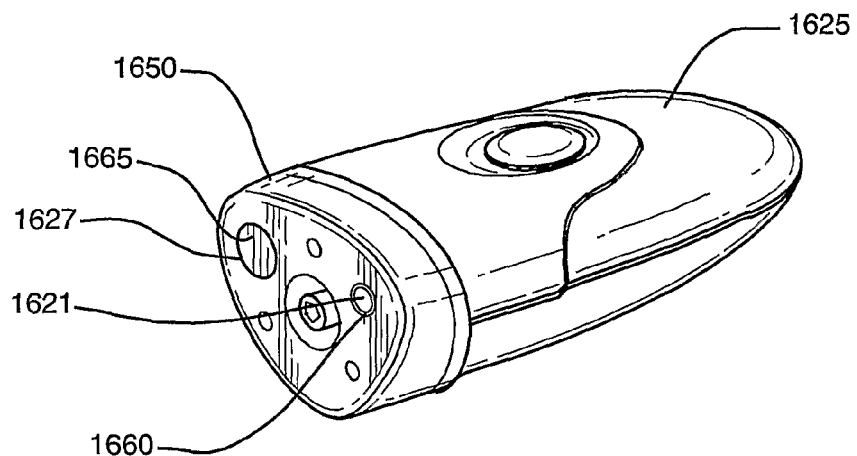
FIG. 16C illustrates a base of a probe of the present invention.
Figure 16D:
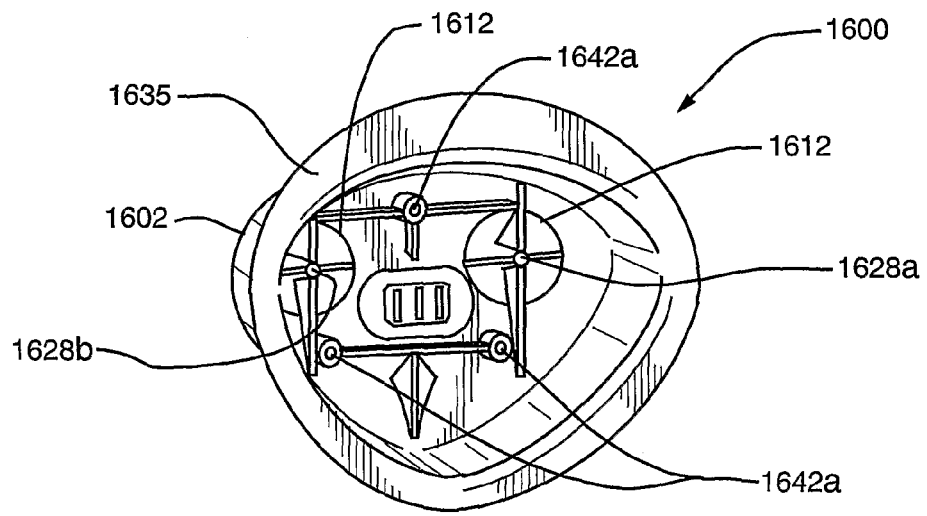
FIGS. 16D and 16E illustrate a light guide assembly of the present invention.
Figure 16E:
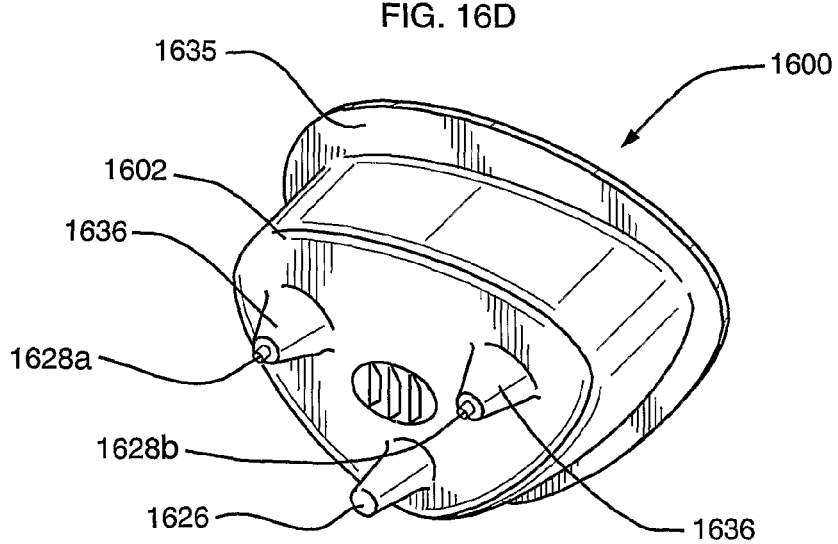
Figure 16F:
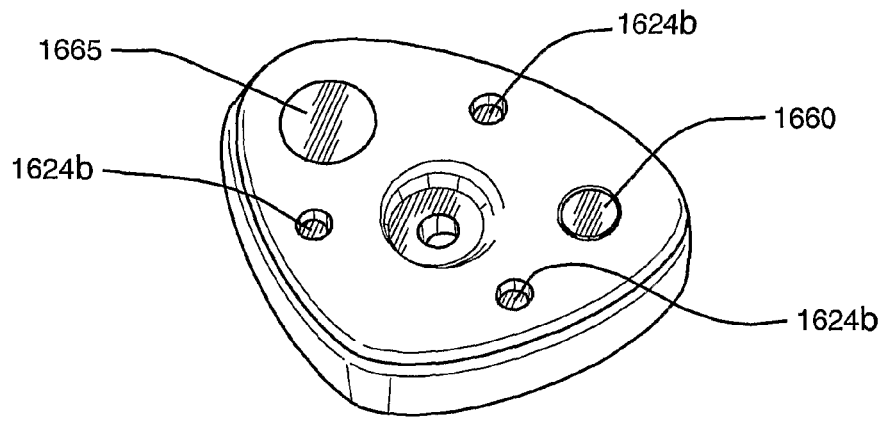
FIG. 16F illustrates a portion of a probe of the present invention.
Figure 16G:
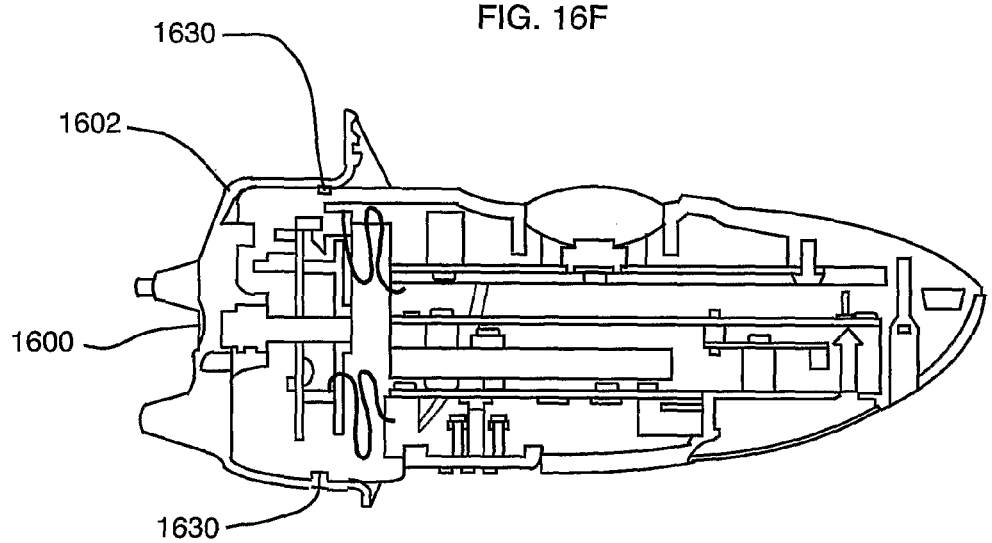
FIG. 16G illustrates a cutaway view of a probe of the present invention.

In one embodiment, light guide assembly 200 is secured to probe 120 by assembly securement 230 (examples of which are illustrated in FIG. 2A, 16D, 16G). In one embodiment (FIG. 2A) assembly securement 230 is a friction fit securement. In an embodiment illustrated in FIG. 2A, friction-fit securement 230 includes apertures 231 within which collars 220 are snuggly-fit. In one embodiment securement 230 is a channel securement 231. In an embodiment illustrated in FIG. 2B, channel securement 231 is configured to accept light guide assembly 200 in an aligned position such that light guides 128 are aligned with light source 121 and detector 127 respectively. In the embodiment illustrated in FIG. 2B, light guides 128 approximately abut covers 235. Covers 235 are preferably configured to protect light source 121 and detector 127 when, for example, light guide assembly 200 is removed (e.g., for disposal between patients as described below) from probe 120 and to permit the transmittance of light during the operation of probe 120. In one embodiment, covers 235 are made of a transparent material such as clear glass or plastic.

In other embodiments, securement 230 includes fasteners such as threaded fasteners, screws, bolts, clips, swivels, straps, tabs, collars or combinations thereof. Preferably securement 230 is configured to permit light guide assembly 200, 1400, 1500, 1600 to be readily removed and replaced on probe 120 between uses with different patients. In one embodiment, such as a trauma setting with multiple patients, light guide assembly 200 is configured to be disposable between patients. In one embodiment, the portions of probe 120 that are intended to contact a patient are configured to be disposable and to act as a protective barrier against contamination of the probe. In one embodiment, light guides are readily detachable from light guide assembly 200 and the light guides themselves are disposable. Preferably, light guide assembly 200, 1400, 1500, 1600 is configured to be removable and replaceable by the operator without any external tools such as a screw driver.

In a preferred embodiment, a user is able to hastily remove used light guide assembly 200 from probe 120 by hand (e.g., without the use of tools), properly dispose of the used light guide assembly 200 and securely replace it with a fresh sterile light guide assembly 200, preferably with little or no consideration to which light guide is meant for alignment with detector 127 or light source 121. In one embodiment, light guide assembly 200 applied in any orientation will function properly. In another embodiment, such as light guide assembly 1600 illustrated in FIGS. 16A, 16B, 16D, 16E, 16I and 16J, will only fit in a manner that properly aligns the light guides with detector 1627 or light source 1621. In this manner, light guide assembly 200, 1400, 1500, 1600 may be replaced in less than one minute or in one embodiment, in a matter of a few seconds by a user of system 100.

One method of detecting a hematoma condition in a plurality of patients includes: providing a detection system having i) at least one radiation detector, ii) at least one light source, iii) at least one radiation detector; iv) at least one processor configured to communicate with the light source and with the radiation detector(s) during the operation of the detection system and v) a first light guide assembly, removably secured to the detection system, having at least one first detector light guide configured to align with the at least one radiation detector and at least one first source light guide configured to align with the at least one light source; operating the detection system, with the first light guide assembly in contact with a patient, to a) transmit light from the at least one light source through the first light guide assembly via the first source light guide and b) detect at least a portion of the transmitted light with the at least one radiation detector after the light has passed through the patient and returned through the first light guide assembly via the first detector light guide; removing the first light guide assembly from the detection system after operating detection system with the first light guide assembly; attaching to the detection system a second light guide assembly having at least one second detector light guide configured to align with the at least one radiation detector and at least one second source light guide configured to align with the at least one light source; and with the second light guide assembly in contact with a second patient, operating the detection system to a) transmit light from the at least one light source through the second light guide assembly via the second source light guide and b) detect at least a portion of the transmitted light with the at least one radiation detector after the light has passed through the second patient and returned through the second light guide assembly via the second detector light guide. As described herein, depending upon the embodiment of the first light guide assembly selected, the first light guide assembly may be disposed of or sterilized for future use. One method of the present invention also includes a method of preparing a hematoma detection probe having a light guide assembly that includes: removing, by hand, a used light guide assembly from the hematoma detection probe; and securing by hand, a replacement sterile light guide assembly to the detection probe. In one embodiment the replacement is without tools. In another embodiment of the method the removing and securing steps are performed serially between patients.

Resiliently Depressible Light Guides. In one embodiment, uniformity of results is affected by the uniformity of pressure that is applied to the light guides as the light guides contact a surface (e.g., a scalp). In one embodiment, there is a probe 120 configured with one or more resiliently depressible light guides 1428 (See FIG. 14A).

In one embodiment, resiliently depressible light guides are configured to apply a uniform pressure against a surface to which resiliently depressible light guides 1428 are applied. In one embodiment, when the light guides are pressed against a scalp, the force being applied to the scalp must not be painful to the patient. In one embodiment, sufficient force must be applied to penetrate hair. In one embodiment, the resiliently depressible light guides 1428 are configured such that the force being applied to resiliently depressible light guides 1428 during use, and therefore to the patient's scalp, is substantially uniform. In one embodiment, the force is between approximately 0.2 N and approximately 3.5 N. In one embodiment, all light guides on probe 120 are resiliently depressible light guides 1428. In another embodiment, probe 120 includes at least one non-resiliently depressible light guide 1459. In one embodiment, illustrated in FIGS. 14A to 14C, interior light guides 1452 are resiliently depressible and exterior light guides 1454 are not resiliently depressible. In one embodiment, the non-resiliently depressible light guides 1459 are in a fixed position relative to light guide assembly 1400. In another embodiment, non-resiliently depressible light guides 1459 are movable (e.g., slidable) relative to light guide assembly 1400 but are not engaged with a bias element or some other means that would confer depressible resilience. In one embodiment, resiliently depressible light guides 1428 move relative to base 1402 (FIG. 14A) and non-resiliently depressible light guides 1459 are rigidly connected to base 1402. In one embodiment, the movement of light guides 1428 relative to base 1402 is a sliding movement relative to base 1402.

In one embodiment, seal 1430 protects detectors 127a, 127b (FIG. 14A). In one embodiment seal 1430 is associated with light guides that move (e.g., slide) relative to base 1402 to protect either detectors 127 or light sources 128 with which the sliding light guide may be associated. In one embodiment, seal 1430 is a flexible seal that is configured to move as resiliently depressible light guide 1428 moves. In one embodiment, seal 1430 is a polyurethane seal. In one embodiment, seal 1430 is fixed to light guide assembly 1400 and is disposed (e.g., with or without light guide assembly 1400) after use.

In one embodiment, each resiliently depressible light guide 1428 is independently resiliently depressible. In another embodiment, at least two resiliently depressible light guides 1428 compress simultaneously. In one embodiment, bias element 1444 is configured to apply a uniform and/or predetermined pressure when resiliently depressible light guide 1428 is applied to a surface to be scanned.

With further reference to FIGS. 14A and 14C, in one embodiment, resiliently depressible light guides 1428 freely slide relative to base 1402 and engage bias structure 1445. In one embodiment, illustrated in FIG. 14C, light guide assembly 1400 does not include bias element 1444 or bias structure 1445. In one such embodiment, light guide assembly 1400 is configured to engage bias structure 1445 (e.g., when it is removably secured to optical bench 1425). In one embodiment, bias structure 1445 is configured to move relative to optical bench 1425. In one embodiment, bias structure 1445 includes bias element 1444 (e.g., a spring) and is configured to bias against resiliently depressible light guides 1428 when light guide assembly 1400 is secured to optical bench 1425. In one embodiment, light guide assembly 1400 is removably secured to optical bench 1425. In one embodiment, light guide assembly 1400 is configured to be disposable. In another embodiment light guide assembly 1400 is configured to be sterilized between uses.

In the embodiment of FIG. 14A, probe 120 includes three detectors 127a, 127b, 127c and one light source 121. Interior detectors 127a, 127b are associated with resiliently depressible light guides 1428. In FIG. 14A, resiliently depressible light guides 1428 do not change length when they are depressed, rather they cause a bias element 1444 (e.g., a spring) to compress resiliently. Upon removal of the force, resiliently depressible light guides 1428 return to their pre-depression state. In FIG. 14A, one outer detector 127c is not associated with a resiliently depressible light guide 128. Also in FIG. 14, light source 121 is not associated with a resiliently depressible light guide.

Figure 15A:
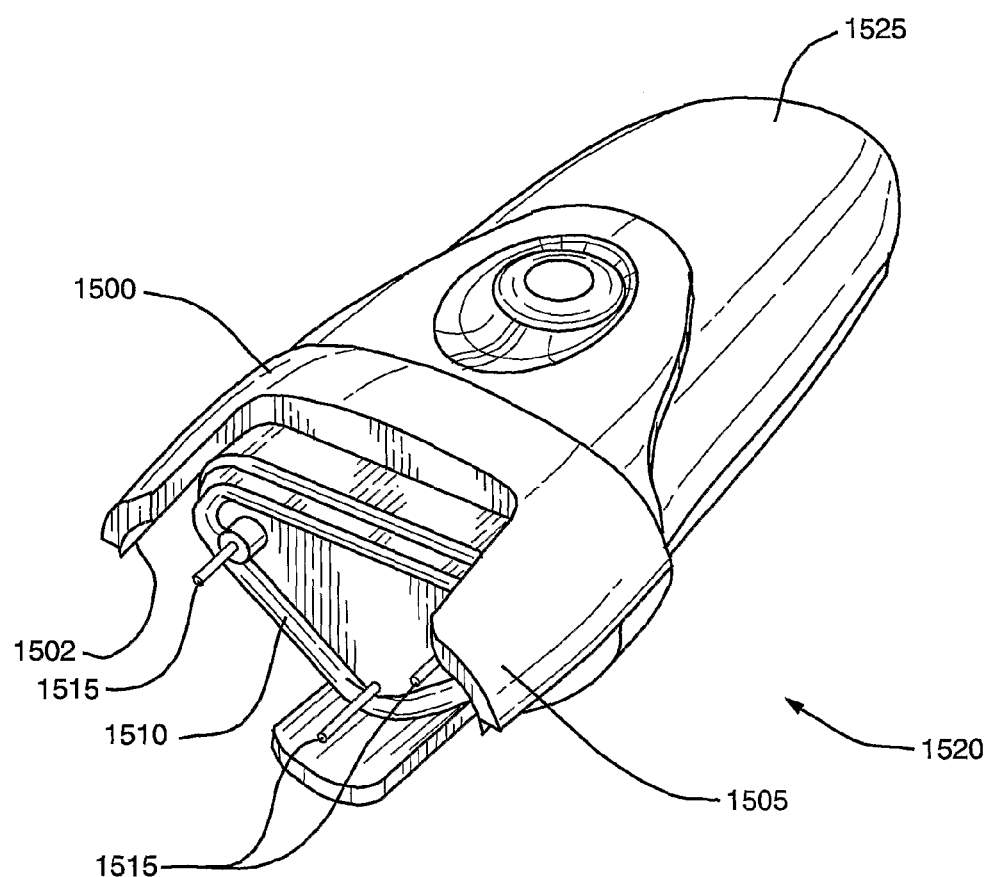
FIG. 15A illustrates a probe of the present invention.
Figure 15B:
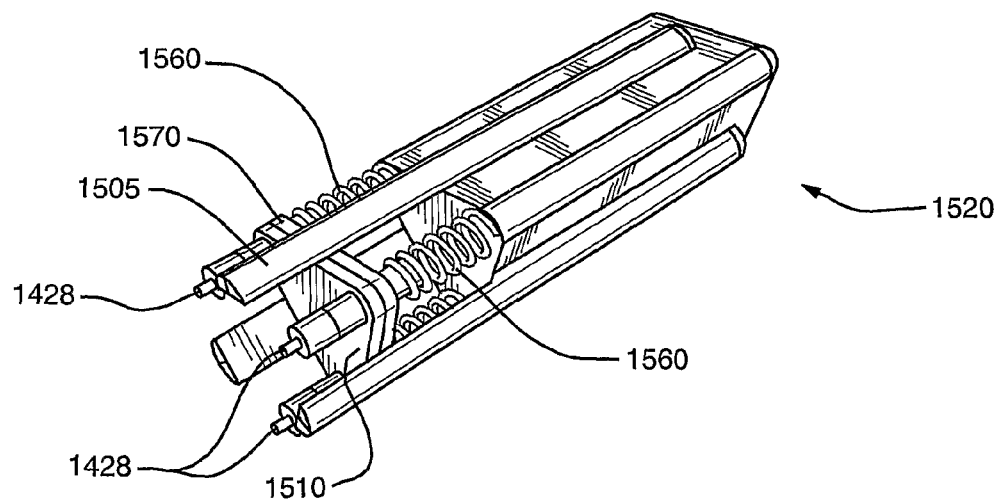
FIG. 15B illustrates a portion of a probe of the present invention.

In one embodiment, illustrated in FIG. 15A, there is a probe 1520 that includes housing 1525 and light guide assembly 1500 that is readily detachable from housing 1525. In one embodiment, light guide assembly 1500 includes frame 1505. In one embodiment, when light guide assembly 1500 is secured to probe 1520, frame 1505 does not move relative to probe 1520. In one embodiment, light guide assembly 1500 includes resiliently depressible light guide platform 1510. In one embodiment, when light guide assembly 1500 is applied to a surface to be tested, frame 1505 rests on the surface (e.g., a scalp) and resiliently depressible light guide platform 1510 retracts against one or more bias elements 1560 within probe 120 (schematically illustrated in FIG. 15B). In one embodiment, light guide assemble 1500 includes resiliently depressible light guides 1428 that are not moveable relative to light guide platform 1510. Also in the embodiment of FIG. 15B, light guide platform 1510 is in direct communication with optical bench 1570. Optical bench 1570 is secured to probe 1520 via bias elements 1560 and is configured to move relative to probe when pressure is applied to a light guide tip(s) 1515. In one embodiment, light guide platform 1510 is does not move relative to optical bench 1570 yet it is resiliently depressible (e.g., is spring-loaded) relative to probe 1520 and to light guide assembly 1500.

Figure 16H:
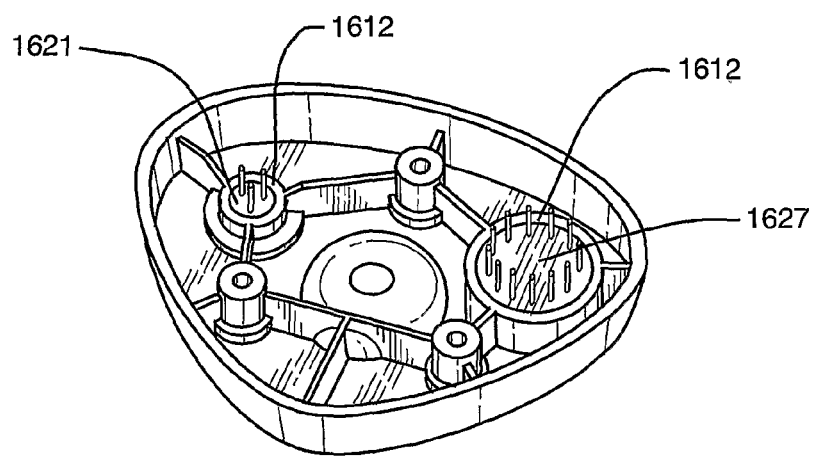
FIG. 16H illustrates a portion of a probe of the present invention.
Figure 16I:
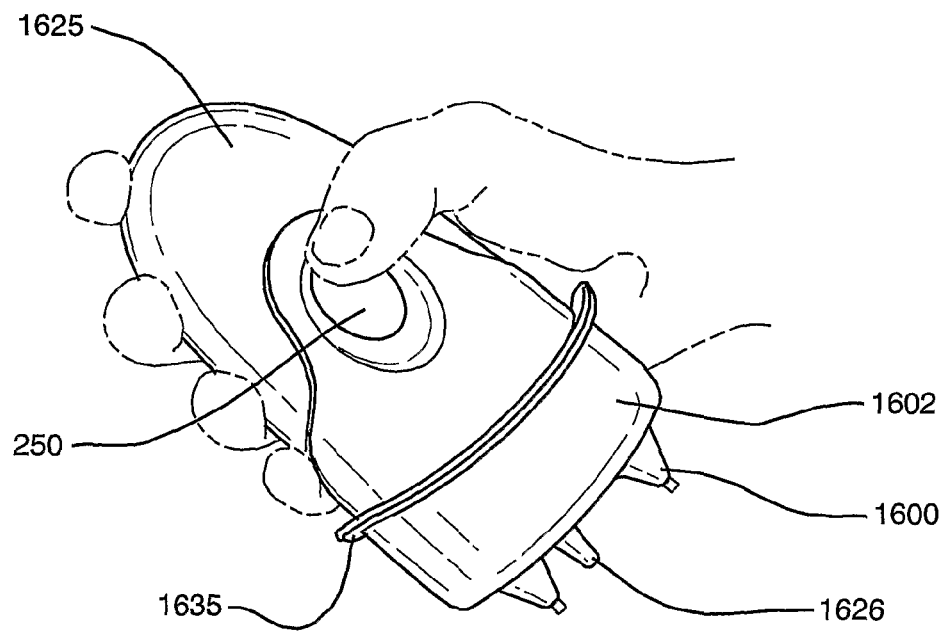
FIGS. 16I and 16J illustrate various views of a probe of the present invention.
Figure 16J:
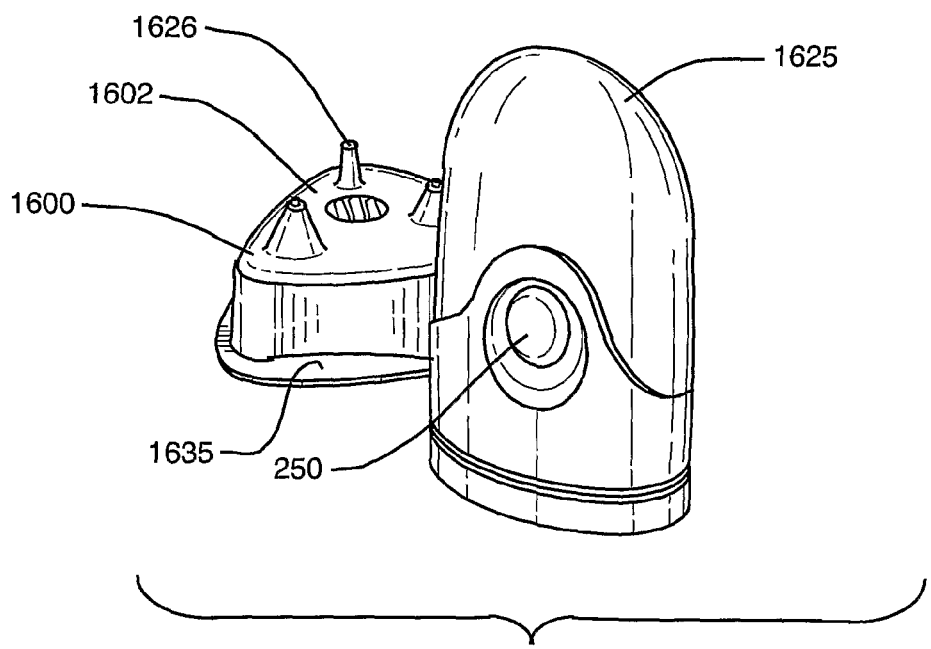

FIGS. 16A-16J illustrate an embodiment of hand-held hematoma detection device 1610 that includes base 1625 and light guide assembly 1600. In one embodiment, base 1625 includes probe circuitry. In another embodiment, base 1625 includes both probe circuitry and processor circuitry. In one embodiment, base 1625 includes at least one radiation detector 1627 and at least one light source 1621 (FIG. 16C). In one embodiment, base 1625 includes measure button 250 (described in more detail below). In one embodiment base 1620 is configured to comfortably fit in a user's hand such that measure button 250 is naturally aligned with one of the user's fingers (e.g., a user's thumb as illustrated in FIG. 16I). FIG. 16B illustrates sealed portal 1616. In one embodiment, sealed portal 1616 is displaceable or removable to reveal power and/or data connection ports.

In one embodiment, light guide assembly 1600 is configured to be disposable. In one embodiment, light guide assembly 1600 is configured to be removed sterilized and replaced on probe 1610. In one embodiment, light guide assembly 1600 includes cover 1602 that is preferably of a substantially rigid one-piece construction. In one embodiment cover 1602 is a molded cover configured to be removably and snuggly fit one end of probe 1610.

In one embodiment, light guide assembly 1600 includes at least one detector light guide 1628a configured to align with the radiation detector 1627 and at least one source light guide 1628b configured to align with the light source 1621. In one embodiment, detector light guide 1628a and source light guide 1628b are cladded (e.g., having an outer layer with a lower index of refraction) light guides. In certain embodiments, detector light guide 1628a and source light guide 1628b are movably or immovably fixed to cover 1602. In one embodiment, cover 1602 and light guide cladding 1636 are contiguous (e.g., of a unitary molded construction).

In one embodiment, light guide assembly 1600 includes lip 1635. In one embodiment, lip 1635 and cover 1602 are contiguous (e.g., of a unitary molded construction). In one embodiment, lip 1635 is located at an end of light guide assembly 1600 opposite where source light guide 1628b and detector light guide 1626a protrude from light guide assembly 1600. In one embodiment, lip 1635 is useful for keeping heavy debris (e.g., blood, mud, dirt, hair, loose tissue on a patient) away from the interface between light guide assembly 1600 and base 1625. In one embodiment, lip 1635 also facilitates the securement of light guide assembly 1600 to base 1625. For example, in a battlefield or other trauma situation where a user's hand may be slippery, lip 1635 provide a structure against which a users hand may be applied to secure light guide assembly 1600 over an end of base 1625 and force light guide assembly 1600 into a locking securement with base 1625. In one embodiment, lip 1635 protrudes laterally from light guide assembly 1600. In one embodiment, the lateral protrusion from light guide assembly 1600 is at least substantially disposed about the entire perimeter of light guide assembly 1600.

In one embodiment (best seen in FIGS. 16D and 16H), light guide assembly 1600 includes at least one light dam 1612 configured to at least substantially block light from propagating from light source 1621 to radiation detector 1627 within the device itself (e.g., thereby reducing the quantity of light that does not propagate to the tissue of interest thereby detracting from the value of readings). In one embodiment, at least one light dam 1612 is radially disposed about at least one of detector light guide 1628a and source light guide 1628b. In one embodiment, each of detector light guide 1628a and source light guide 1628b includes an independent light dam 1612. The embodiment of FIG. 16D illustrates two light dams 1612, one associated with detector light guide 1628a and a second associated with source light guide 1628b. Other embodiments include only one light dam. In one embodiment, as illustrated in FIG. 16D, at least one light dam 1612 is integral with light guide assembly 1600 and is configured to engage base 1625 when light guide assembly 1600 is secured to base 1625 thereby at least substantially sealing one or both of detector light guide 1628a and source light guide 1628b from the other. In one embodiment, light dams 1612 are contiguous (e.g., in a unitary molded construction) with cover 1602.

In one embodiment, light guide assembly 1600 is configured to align with base 1625 such that a detector light guide 1628a aligns with radiation detector 1627 and light source 1621. In one embodiment, the alignment is unique such that an operator of device 1628a working in haste cannot inadvertently apply light guide assembly 1600 to base 1625 incorrectly. In one embodiment, light guide assembly 1600 includes one or more assembly alignment features 1642a that are configured to match one or more base alignment features 1642b. In one embodiment, the rounded triangular cross section of base 1625 and light guide assembly 1600 facilitate rapid and accurate connection between light guide assembly 1600 and base 1625.

In one embodiment, friction between assembly alignment features 1642a and base alignment features 1642b are configured to at least partially secure light guide assembly 1600 to base 1625 (e.g., by friction). In one embodiment, when light guide assembly 1600 is secured to base 1625, source light guide 1628b is oriented very close to or touching source laser window 1660. In one embodiment, detector light guide 1628a is very close to or touching detector filter 1665 when light guide assembly 1600 is secured to base 1625.

In one embodiment, hand-held hematoma detection device 1610 includes a sealed securement between base 1625 and light guide assembly 1600. In one embodiment, the securement includes seal 1630 (e.g., as shown in FIG. 16G). In one embodiment, seal 1630 prevents unwanted media (e.g., blood, mud, water, dirt) from contaminating laser window 1660 and/or detector filter 1665.

In one embodiment, probe 1620 includes a securement means for removably securing light guide assembly 1600 to base 1625 in such a way as to promote proper alignment of light guides 1628b, 1628a with light source 1621 and detector 1627 respectively, and for sealing light guide assembly 1600 to base 1625. In one embodiment, the securement means also includes alignment features 1624a.

In the embodiment of FIG. 16C, optical bench 1650 is shown attached to base 1625. FIG. 16H illustrates detector 1627 and light source 1621 in mounting positions relative to optical bench 1650. Optical bench 1650, in some embodiments, includes at least one light dam 1612 that substantially completely optically isolates detector 1627 from light source 1621 within optical bench 1650. Optical bench 1650, in some embodiments, includes at least one light dam 1612 that substantially completely optically isolates light source 1621 from detector 1627 within optical bench 1650.

In one embodiment, hand-held hematoma detection device 1610 includes at least one external support 1626 (FIGS. 16A, 16B, 16E, 16I, 16J). In one embodiment, the at least one external support 1626 is a frame (e.g., frame 1505, FIG. 15A). In one embodiment, external support 1626 is an inert external support that protrudes from light guide assembly 1600. In one embodiment, external support 1626 enables a user to steady the hand-held hematoma detection device 1610 against a subject's scalp such that light guide assembly 1600 is oriented substantially uniformly relative to the scalp among the different readings. In one embodiment, external support 1626 facilitates a substantially perpendicular orientation between detector light guide 1628a and the scalp and/or source light guide 1628b and the scalp. In one embodiment, external support 1626 is an external protrusion that protrudes a distance from light guide assembly 1600 that is substantially equivalent to the distance that light guides (e.g., source light guide 1628b and detector light guide 1626a) protrude from light guide assembly 1600. In one embodiment, external support 1626 is spaced equally between source light guide 1628b and detector light guide 1626a. In one embodiment, external support 1626 is contiguous with cover 1602 (e.g., a unitary molded construction). In one embodiment cover 1602 includes lip 1635, at least one light dam 1612, at least one external support 1626 and cladding 1636. In one embodiment cover 1602 is of a unitary molded construction.

General Method of Operation

In an embodiment of the present invention, the method of determining intracranial hematoma is based upon the principle that extravascular blood exhibits a different optical density than intravascular blood. In one embodiment, the difference in optical density is attributable to a difference in concentration between extravascular and intravascular blood.

In one embodiment of the present invention, a wavelength is selected wherein the concentration of oxygen in blood and/or tissue is substantially not a factor in the diagnosis of hematoma. At a wavelength of approximately 800 nm to approximately 810 nm, for example, NIR radiation is absorbed substantially equally as between tissue having differing magnitudes of oxygen in blood. In one embodiment of the present invention, at a wavelength of between approximately 800 nm and 810 nm and preferably at 808 nm, the difference in optical density is substantially attributable to differing accumulations of blood in tissue. Since larger accumulations of blood are indicative of the presence of extravascular blood, a diagnosis of hematoma in one embodiment is more reliable when it is based substantially exclusively on volumetric considerations than if the diagnosis were being influenced both by the volume of localized blood accumulation and differing oxygenation levels in the target tissue.

In one embodiment of operation, light source 121 and detector 127 are optically coupled (e.g., as illustrated in FIG. 1C) to a patient's head through light guides 128. In one embodiment, light source 121 emits light in a wavelength compatible with detector 127 located a fixed distance away. Detector 127 detects diffuse light emanating from light source 121 via light guide 128 and the tissue of interest. The signal from detector 127 is then transmitted, preferably after being digitized, to processor 140 from which an operator of system 100 can monitor both the progress of data collection and the results.

In a preferred method of the present invention, light guides 128 of probe 120 are placed against a patient's head (and preferably positioned such that hair is not trapped between light guide 128 and the patient's skin) at one of eight lobe locations: right frontal, left frontal, right temporal, left temporal, right parietal, left parietal, right occipital, and left occipital as illustrated in FIGS. 1A and 1B. In the embodiment illustrated in FIGS. 1A and 1B, light guides 128 of probe 120 are positioned within each of the eight lobe locations such that the light guide 128a associated with light source 121 and the light guide 128b associated with detector 127 are each positioned at a skull location corresponding with the lobe of interest. In one embodiment, this ensures that the measurement of detector 127 reflects the optical density of only one tissue location. In one embodiment, the positioning of probe 120 requires that the probe be located with a precision of approximately between 1 cm and 3 cm of the desired location. In one embodiment, light guides 128 must be positioned substantially normal to a patient's head.

In one embodiment, light emitted from light source 121, at a selected wavelength (e.g., approximately 808 nm+/−approximately 3 nm) propagates through light guide 128 to tissue in one of the eight lobe locations. A portion of the photons emitted from light source 121 are detected by detector 127 via light guide 128. In one embodiment, the measurement procedure is repeated for each of the patient's remaining seven (7) lobes, as described in more detail below. In one embodiment, both unilateral and bilateral hematoma may be detected on the basis of the measurements taken.

In one embodiment, detector 127 transduces the detected light at each measurement location to an electrical signal which is digitized by the circuitry in probe 120. In one embodiment, a measured signal intensity (I) is then determined for each measurement location, for example, using Eq. 1, as the logarithm of the product of light source power, detector gain, and integration time divided by the voltage of detector 127.

The difference in optical density (ΔOD) between a first tissue location and a second tissue location is determined based upon a comparison of the measured signal intensity between the first and second tissue locations.

Thus:

$$\Delta OD = I_1 - I_2; I = \log_{10}[100 \times power \times gain/V_{det}] \quad (1)$$

In an embodiment of the equation illustrated in Eq. 1, the factor of 100 is added to compensate for different units (power in mV, gain in arbitrary units, detector voltage in mV) and to normalize the OD values within the range of 1 to 5.

In one embodiment, the measured detector voltage $V_{det}$ for each measurement is the difference between the signal with light source 121 on and the dark current measurement. (e.g., real time dark current subtraction). In one embodiment, the power value is the actual power of light source 121 for the particular measurement, normalized by the relevant value from a light source calibration table (discussed in more detail below) to compensate for non-linearity of system 100 circuitry. In one embodiment, the gain value of detector 127 is also normalized by a calibration table (discussed in more detail below). In another embodiment, detector gain is tested for linearity and then, only if gain is linear, will a calibration process for gain be eliminated.

In one embodiment, the OD will be higher for tissue with higher absorption and lower for tissue with lower absorption (e.g., lower attenuation of light being emitted from light source 121). In one embodiment, the order in which tissue is tested is determines whether ΔOD will be positive or negative. A diagnosis of a hematoma condition, in one embodiment, is based upon whether ΔOD is positive or negative. In one embodiment, the absolute value of ΔOD is used to diagnose a hematoma condition. In one embodiment, the absolute value of ΔOD and whether that value is positive or negative are both relevant to the diagnose of a hematoma condition.

Figure 5B:
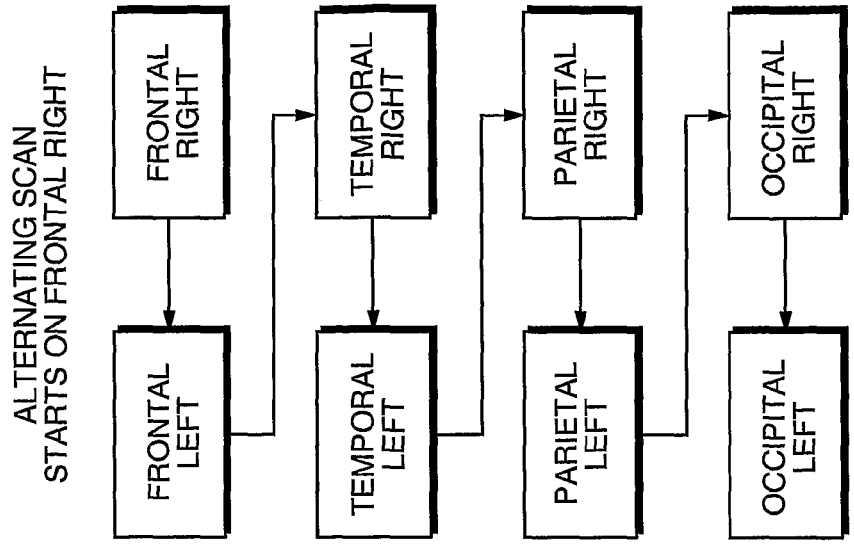
FIGS. 5A-5D illustrates embodiments of detection methods of the present invention.
Figure 5A:
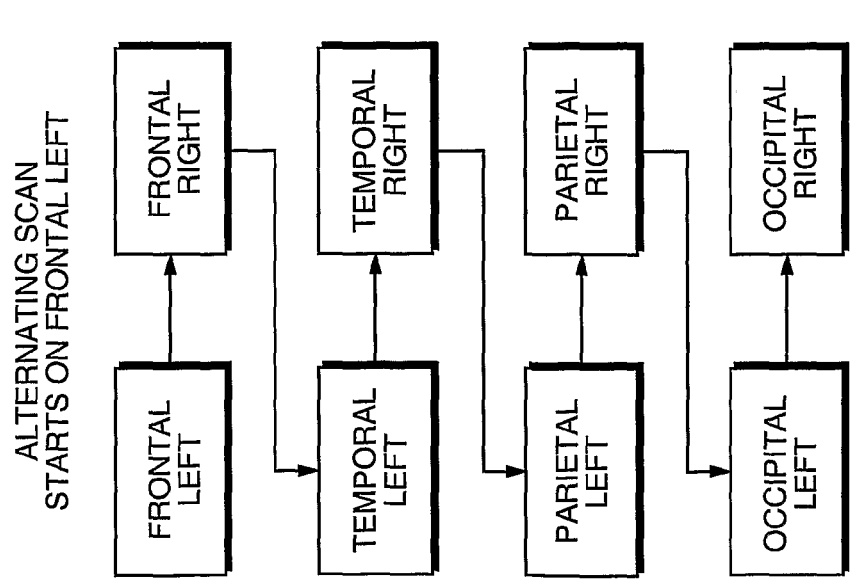
Figure 5D:
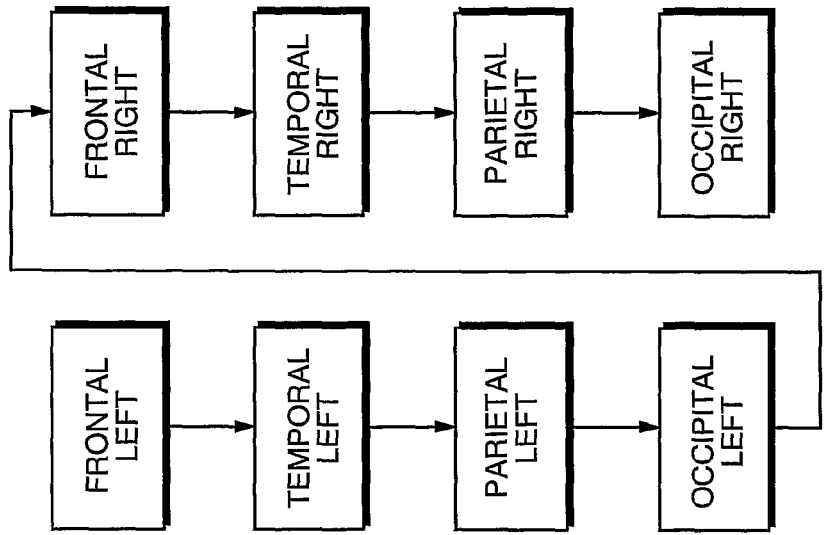
Figure 5C:
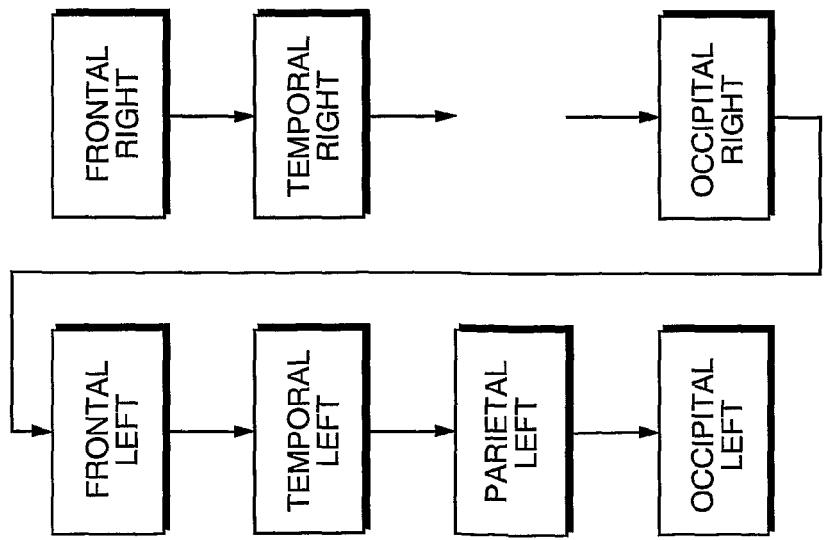

In one embodiment the four tissue locations on either side of a patient's head can be tested in any order. In an embodiment illustrated in FIG. 5A, eight tissue locations (four on each side of a patient's head) are tested by alternating between the right and left sides of the brain, starting with Frontal Left and then proceeding to Frontal Right, Temporal Left, Temporal Right, Parietal Left, Parietal Right, Occipital Left and finally Occipital Right. In another embodiment, illustrated in FIG. 5B, brain tissue is scanned by alternating between the left and right sides of the head staring with Frontal Right and proceeding in order to Frontal Left, Temporal Right, Temporal Left, Parietal Right, Parietal Left, Occipital Right and Occipital Left. In another embodiment, illustrated in FIGS. 5C and 5D, the four (4) tissue locations on one side of the head are tested before moving to the contralateral head locations. In one embodiment, as in FIG. 5C, the Frontal Right lobe is tested first, and then proceeding to Temporal Right, Parietal Right, Occipital Right, Frontal Left, Temporal Left, Parietal Left and Occipital Left. Similarly, as illustrated in FIG. 5D, the Frontal Left Tissue is tested first, and then proceeding to Temporal Left, Parietal Left, Occipital Left, Frontal Right, Temporal Right, Parietal Right, and Occipital Right.

In one embodiment ΔOD is measured between contralateral head locations, i.e., Right Frontal v. Left Frontal, Right Temporal v. Left Temporal, Right Occipital v. Left Occipital and Right Parietal v. Left Parietal). In one embodiment, probe 120 is placed in a substantially identical location on opposing sides of patient's head (i.e., a symmetric placement) for a particular contralateral pair. In another embodiment, the placement of probe 120 relative to opposing brain lobes is within approximately 1 cm to approximately 3 cm of being symmetric on both sides of the patient's head.

In one embodiment, there is a method of indicating a hematoma condition. The method, in one embodiment, includes determining an optical density difference for at least one pair of contralateral head locations; comparing said optical density difference to a predetermined range of optical density differences; and diagnosing a hematoma condition in each of the contralateral head locations based upon the relationship between the optical density difference and the predetermined range of optical density differences. There is also an embodiment wherein the predetermined range of optical density differences is between −0.1 and 0.1. There is another embodiment wherein the predetermined range is taken from the group consisting of −0.3 to −0.1, +0.1 to +0.3 and combinations thereof. In one embodiment, the hematoma condition is taken from the group consisting of no hematoma, possible hematoma and hematoma. There is another embodiment wherein diagnosing a hematoma condition includes diagnosing the possibility of hematoma when an absolute value of the optical density difference is between 0.1 and 0.3. There is yet another embodiment wherein the diagnosing a hematoma condition includes diagnosing hematoma when an absolute value of the optical density difference is greater than 0.3.

In one embodiment, a method of indicating a hematoma condition includes: determining an optical density associated with each of a patient's frontal lobes, temporal lobes, occipital lobes and parietal lobes; determining a frontal lobe optical density difference; determining a temporal lobes optical density difference; determining an occipital lobe optical density difference; determining a parietal lobe optical density difference; and indicating hematoma at one or more of a patient's frontal, temporal, occipital and parietal lobes based upon a comparison between the optical density differences and at least one predetermined range of optical density differences.

In one embodiment, a hematoma condition is diagnosed based upon the value of ΔOD as between contralateral head locations. In one embodiment, diagnosis of no hematoma is made if ΔOD between contralateral head locations has an absolute value of less than a predetermined value, X. In one embodiment, X is approximately 0.1. In one embodiment, hematoma is diagnosed when the absolute value of ΔOD between contralateral head locations is above a predetermined value, Y. In one embodiment, Y is approximately 0.3. In one embodiment, the possibility of hematoma is diagnosed when the absolute value of ΔOD is between two predetermined values, W and Z. In one embodiment, W is approximately 0.1 and Z is approximately 0.3.

Figure 6:
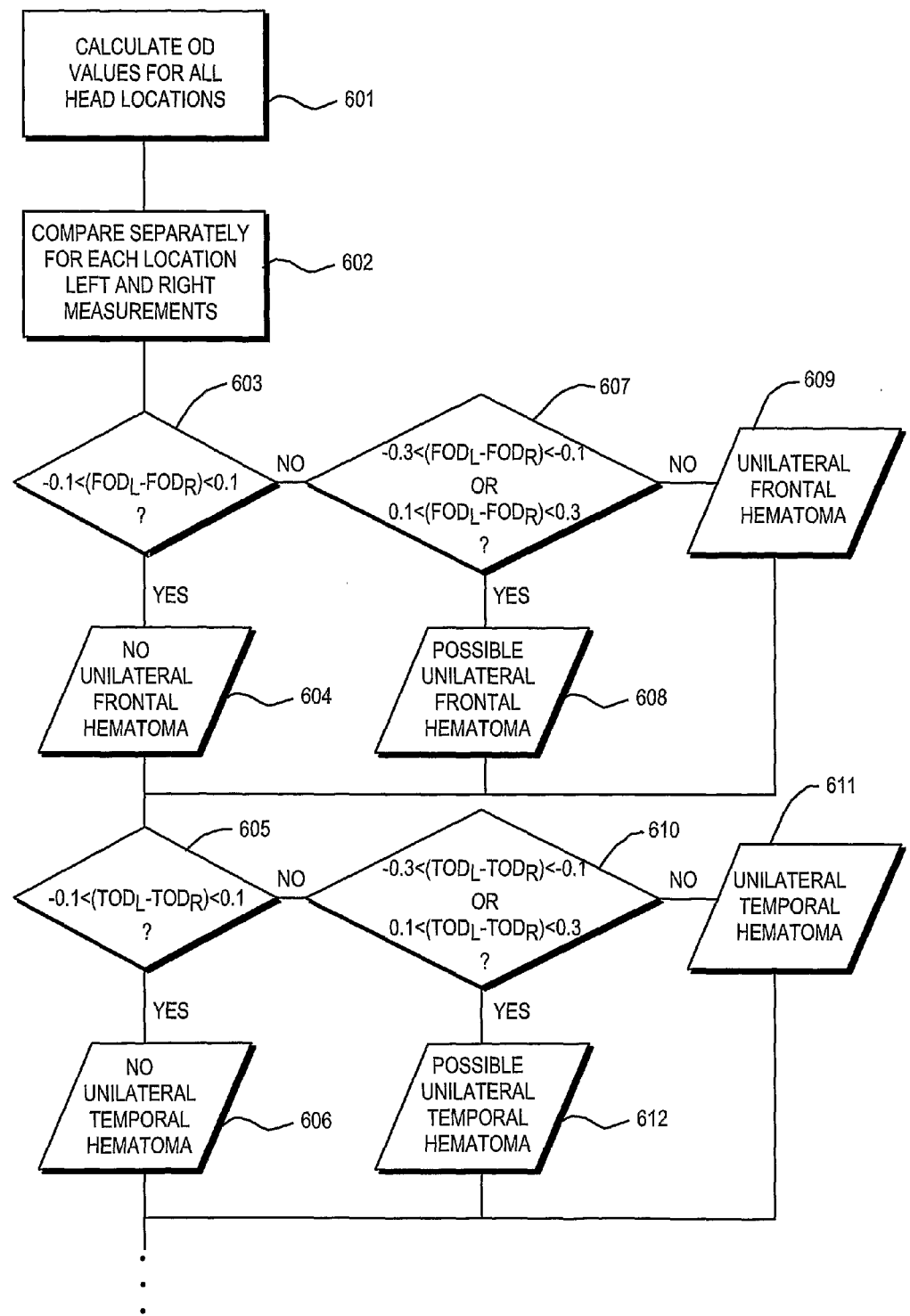
FIG. 6 illustrates an embodiment of a method of brain hematoma detection calculation of the present invention.

Thus, illustrated in FIGS. 6 and 7, there are embodiments of methods for detection of hematoma and/or possible hematoma using, for example, system 100. In step 601, OD Is calculated for each of eight head locations, for example, as described herein. In step 602 OD measurements at each contralateral head location pair is compared. In the example illustrated in FIG. 6, frontal hematoma is diagnosed first, and then temporal hematoma is diagnosed followed by parietal and occipital. Although only the flow chart for frontal hematoma and temporal hematoma are illustrated here, in one embodiment, occipital hematoma and parietal hematoma are diagnosed in a likewise matter. Moreover, in one embodiment, the four lobe locations may be analyzed in any order.

Referring again to FIG. 6, at step 603, if ΔOD between Left Frontal and Right Frontal (i.e., $FOD_L - FOD_R$) has an absolute value of less than 0.1 (i.e., $-0.1 < FOD_L - FOD_R < 0.1$), no unilateral frontal hematoma is indicated (step 604).

If the absolute value of ΔOD at step 603 is greater than 0.1 and less than 0.3 (step 607) then the possibility of frontal unilateral hematoma exists (see step 608). In the embodiment of FIG. 6, OD for the right side of the head is subtracted from OD of the left side of the head. In the embodiment of FIG. 6, if ΔOD is negative at step 607, the possible unilateral frontal hematoma is right frontal hematoma. Conversely, in the embodiment of FIG. 6, if ΔOD at step 607 is positive, the possible unilateral frontal hematoma is left frontal hematoma. If the absolute value of ΔOD at step 607 is greater than 0.3, unilateral frontal hematoma is diagnosed (see step 609); on the right side if ΔOD is negative and on the left side if ΔOD is a positive number. Temporal hematoma is similarly diagnosed in steps 605, 606, 610, 611 and 612 of FIG. 6.

In one embodiment of the present invention, bilateral hematoma is diagnosed by calculating both ΔOD for contralateral pairs (e.g., right frontal v. left frontal, right temporal v. left temporal and so on) and ΔOD for all combinations of lobes for one side of the head (e.g., right frontal v. right temporal, right frontal v. right occipital, right frontal v. right parietal and so on). In one embodiment, system 100 is used to determine, for each side of the patient's head, a frontal/temporal optical density difference (i.e., ΔOD between Frontal Right and Temporal Right, and ΔOD between Frontal Left and Temporal Left) a frontal/parietal optical density difference, a frontal/occipital optical density difference, a temporal/parietal optical density difference, a temporal/occipital optical density difference, and a parietal/occipital optical density difference.

In one embodiment, bilateral hematoma is indicated for at least one of a patient's frontal, temporal, occipital and parietal lobes based upon a comparison between a predetermined optical density difference in two of the lobes and a measured optical density difference in the lobes. For example, in one embodiment, the presence of bilateral hematoma is detectable based upon a comparison between: i) a predetermined frontal/temporal optical density difference range and the measured frontal/temporal optical density differences; ii) a predetermined frontal/parietal optical density difference range and the measured frontal/parietal optical density differences; iii) a predetermined frontal/occipital optical density difference range and the measured frontal/occipital optical density differences; iv) a predetermined temporal/parietal optical density difference range and the measured temporal/parietal optical density differences; and v) a predetermined temporal/occipital optical density difference range to the measured temporal/occipital optical density differences.

In one embodiment, normal tissue has an absolute value of ΔOD in a predetermined range between a value a and a value b when comparing the OD for frontal tissue and temporal tissue on the same side of the head. In another embodiment, normal tissue has an absolute value of ΔOD in a predetermined range of between c and d when comparing the OD for frontal tissue and parietal tissue on the same side of the head. In another embodiment, normal tissue has an absolute value of ΔOD in a predetermined range of between e and f when comparing the OD for frontal tissue and occipital tissue on the same side of the head. Similarly, normal tissue has an absolute value of ΔOD in a predetermined range between a value g and a value h when comparing the OD for temporal tissue and parietal tissue for the same side of the head. In another embodiment, normal tissue has an absolute value of ΔOD in a predetermined range of between i and j when comparing the OD for temporal and occipital tissue on the same side of the head. In yet another embodiment, normal tissue has an absolute value of ΔOD in a predetermined range of between k and l when comparing the OD for parietal tissue and occipital tissue on the same side of the head. In one embodiment, system 100 includes a database that is populated with all of the predetermined ranges.

In one embodiment, the range of absolute values between a and b, c and d, e and f, g and h, i and j, and between k and l is the same range. In one embodiment, one or more of the range of values between a and b, c and d, e and f, g and h, i and j, and between k and l are different than one or more other range values. In one embodiment, the magnitude of one or more of the ranges (e.g., a to b, c to d, e to f, g to h, i to j, and k and l) are different. In another embodiment, the magnitude of one or more of the ranges (e.g., a to b, c to d, e to f, g to h, i to j, and k and l) is substantially the same. In one embodiment the ranges a to b, c to d, e to f, g to h, i to j, and k and l are all within the range of 0 to 3. In another embodiment, the ranges a to b, c to d, e to f, g to h, i to j, and k and l are all within the range of 0 to 2. In yet another embodiment, the ranges a to b, c to d, e to f, g to h, i to j, and k and l are all within the range of 0 to 1. In still another embodiment, the ranges a to b, c to d, e to f, g to h, i to j, and k and l are all within the range of 1 to 2. In still another embodiment, the ranges a to b, c to d, e to f, g to h, i to j, and k and l are all within the range of 2 to 3.

In one embodiment, there is a method of indicating a bilateral hematoma condition that includes determining an optical density associated with a plurality of brain locations on a right side of a patient's head; determining a first optical density difference between two of the plurality of brain locations on the right side of the patient's head; determining an optical density associated with a plurality brain locations on a left side of the patient's head; determining a second optical density difference between two of the plurality of brain locations on the left side of the patient's head; and indicating bilateral hematoma based upon a comparison of the first optical density difference and the second optical density difference to a predetermined optical density difference range.

Figure 7A:
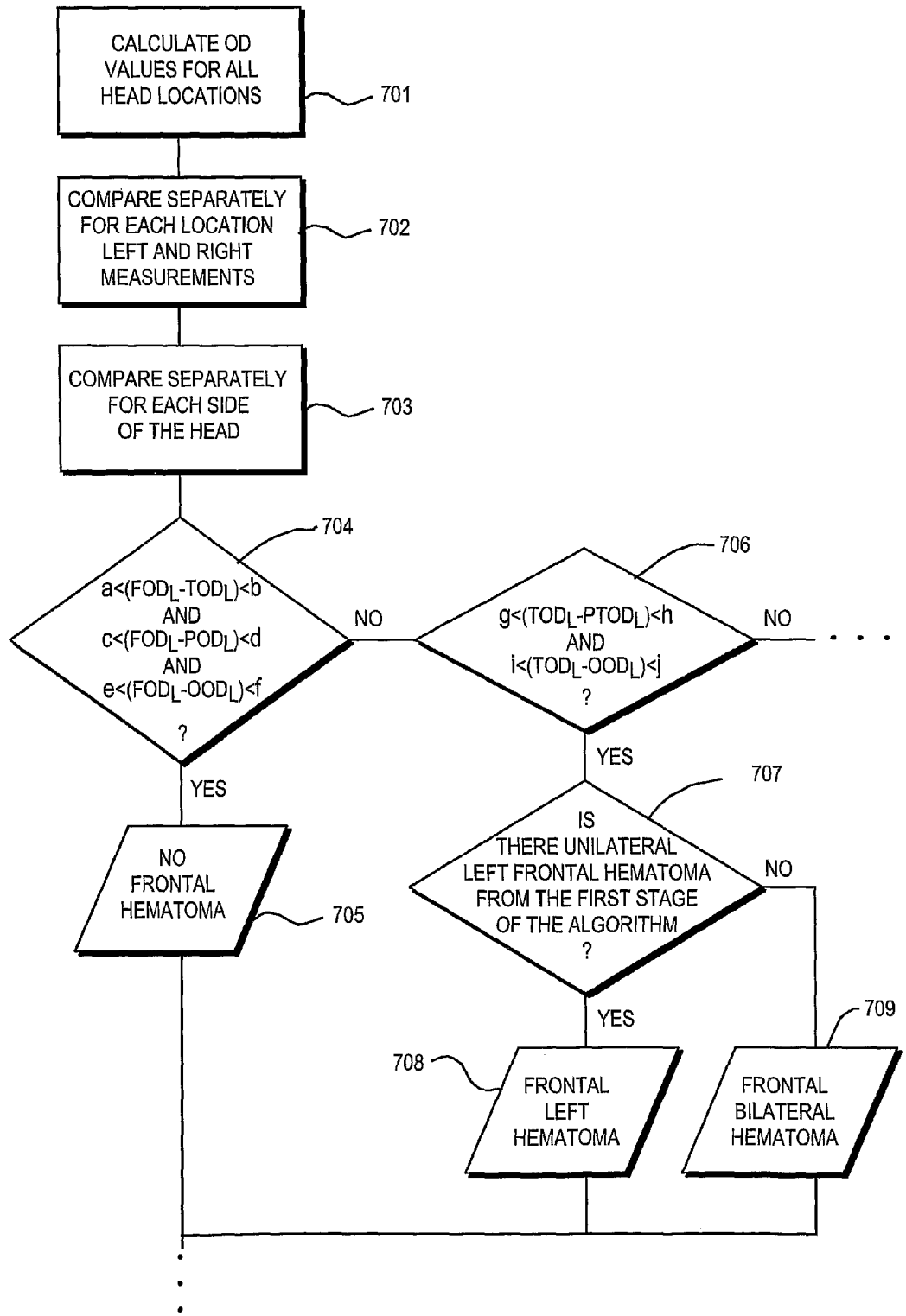
FIG. 7A illustrates an embodiment of a method of brain hematoma detection calculation of the present invention.

FIG. 7A illustrates an exemplary embodiment of one method for determining bilateral hematoma. FIG. 7A illustrates an algorithm involving the left side of the head. In other embodiments, an analogous process may be performed for the right side of the head. In step 701 OD values for all head locations are determined. In step 702 of the embodiment illustrated in FIG. 7A, ΔOD is determined for each contralateral pair such as in step 602 of FIG. 6. In step 703 of the method of FIG. 7A, ΔOD is determined for each of six combinations of head locations (i.e., Frontal/Temporal, Frontal/Parietal, Frontal/Occipital, Temporal/Parietal, Temporal/Occipital and Parietal/Occipital) for each side of the head. For example, in step 704, a determination is made as to whether: i) the left side Frontal/Temporal OD difference is between the predetermined values a and b; ii) the left side Frontal/Parietal OD difference is between the predetermined values c and d; and iii) the left side Frontal/Occipital difference is between the predetermined values e and f. If each of conditions i) to iii) above exist then no frontal hematoma is diagnosed (step 705). If all of conditions i) to iii) do not exist, and condition iv), the left side Temporal/Parietal OD difference being between the predetermined values g and h, and condition v), the left side Temporal/Occipital OD difference is between the predetermined values i and j (step 706), then step 707 is performed. If at step 707 it has been previously determined that unilateral left frontal hematoma has been diagnosed by, for example, the method embodied in FIG. 6, then bilateral hematoma is not diagnosed. If, however, according to the embodiment of FIG. 7A, unilateral left frontal hematoma was not diagnosed prior to step 707 then frontal bilateral hematoma is diagnosed.

In one embodiment, if the conditions of step 706 are not met (e.g., normal conditions do not exist), then the ΔOD difference between left parietal and left occipital is compared to a predetermined range of k and l. Similarly to steps 707-709, if the ΔOD for left occipital and left parietal is in the normal range and there is no left temporal hematoma, then bilateral temporal hematoma is diagnosed. If, however, ΔOD for left occipital and left parietal is in the normal range and there is no bilateral hematoma diagnosed for this patient. In one embodiment, where unilateral hematoma is diagnosed on the right side, the method embodied in FIG. 7A is repeated for the right side lobe combinations.

One method of indicating a bilateral hematoma condition that includes determining an optical density associated with each of a patient's frontal lobes, temporal lobes, occipital lobes and parietal lobes; for each side of the patient's head determining a frontal/temporal optical density difference a frontal/parietal optical density difference, a frontal/occipital optical density difference, a temporal/parietal optical density difference, a temporal occipital optical density difference, and a parietal/occipital optical density difference; indicating bilateral hematoma for at least one of the patient's frontal, temporal, occipital and parietal lobe pairs based upon a comparison between a predetermined frontal/temporal optical density difference range to the frontal/temporal optical density differences, a predetermined frontal/parietal optical density difference range to the frontal/parietal optical density differences, a predetermined frontal/occipital optical density difference range to the frontal/occipital optical density difference, a predetermined temporal/parietal optical density difference range to the temporal/parietal optical density difference, and a predetermined temporal/occipital optical density difference range to the temporal/occipital optical density difference.

In one embodiment, the predetermined frontal/temporal optical density difference range is taken from the group consisting of greater than 0 and less than 3, greater than 0 and less than 2.5, greater than 0 and less than 2.0, greater than 0 and less than 1.5, greater than 0 and less than 1.0, greater than 0 and less than 0.5, greater than 0.5 and less than 3, greater than 0.5 and less than 2.5, greater than 0.5 and less than 2.0, greater than 0.5 and less than 1.5, greater than 0.5 and less than 1.0, greater than 1 and less than 3, greater than 1 and less than 2.5, greater than 1 and less than 2.0, greater than 1 and less than 1.5, greater than 1.5 and less than 3, greater than 1.5 and less than 2.5, greater than 1.5 and less than 2.0, greater than 2 and less than 3, greater than 2 and less than 2.5, and greater than 2.5 and less than 3.

In one embodiment, the predetermined frontal/parietal optical density difference range is taken from the group consisting of greater than 0 and less than 3, greater than 0 and less than 2.5, greater than 0 and less than 2.0, greater than 0 and less than 1.5, greater than 0 and less than 1.0, greater than 0 and less than 0.5, greater than 0.5 and less than 3, greater than 0.5 and less than 2.5, greater than 0.5 and less than 2.0, greater than 0.5 and less than 1.5, greater than 0.5 and less than 1.0, greater than 1 and less than 3, greater than 1 and less than 2.5, greater than 1 and less than 2.0, greater than 1 and less than 1.5, greater than 1.5 and less than 3, greater than 1.5 and less than 2.5, greater than 1.5 and less than 2.0, greater than 2 and less than 3, greater than 2 and less than 2.5, and greater than 2.5 and less than 3.

In a further embodiment of the method the predetermined frontal/occipital optical density difference range is taken from the group consisting of greater than 0 and less than 3, greater than 0 and less than 2.5, greater than 0 and less than 2.0, greater than 0 and less than 1.5, greater than 0 and less than 1.0, greater than 0 and less than 0.5, greater than 0.5 and less than 3, greater than 0.5 and less than 2.5, greater than 0.5 and less than 2.0, greater than 0.5 and less than 1.5, greater than 0.5 and less than 1.0, greater than 1 and less than 3, greater than 1 and less than 2.5, greater than 1 and less than 2.0, greater than 1 and less than 1.5, greater than 1.5 and less than 3, greater than 1.5 and less than 2.5, greater than 1.5 and less than 2.0, greater than 2 and less than 3, greater than 2 and less than 2.5, and greater than 2.5 and less than 3.

In yet another embodiment of the method, the predetermined temporal/parietal optical density difference range is taken from the group consisting of greater than 0 and less than 3, greater than 0 and less than 2.5, greater than 0 and less than 2.0, greater than 0 and less than 1.5, greater than 0 and less than 1.0, greater than 0 and less than 0.5, greater than 0.5 and less than 3, greater than 0.5 and less than 2.5, greater than 0.5 and less than 2.0, greater than 0.5 and less than 1.5, greater than 0.5 and less than 1.0, greater than 1 and less than 3, greater than 1 and less than 2.5, greater than 1 and less than 2.0, greater than 1 and less than 1.5, greater than 1.5 and less than 3, greater than 1.5 and less than 2.5, greater than 1.5 and less than 2.0, greater than 2 and less than 3, greater than 2 and less than 2.5, and greater than 2.5 and less than 3.

In one embodiment, the predetermined temporal/occipital optical density difference range is taken from the group consisting of greater than 0 and less than 3, greater than 0 and less than 2.5, greater than 0 and less than 2.0, greater than 0 and less than 1.5, greater than 0 and less than 1.0, greater than 0 and less than 0.5, greater than 0.5 and less than 3, greater than 0.5 and less than 2.5, greater than 0.5 and less than 2.0, greater than 0.5 and less than 1.5, greater than 0.5 and less than 1.0, greater than 1 and less than 3, greater than 1 and less than 2.5, greater than 1 and less than 2.0, greater than 1 and less than 1.5, greater than 1.5 and less than 3, greater than 1.5 and less than 2.5, greater than 1.5 and less than 2.0, greater than 2 and less than 3, greater than 2 and less than 2.5, and greater than 2.5 and less than 3.

In a further embodiment, the predetermined parietal/occipital optical density difference range is taken from the group consisting of greater than 0 and less than 3, greater than 0 and less than 2.5, greater than 0 and less than 2.0, greater than 0 and less than 1.5, greater than 0 and less than 1.0, greater than 0 and less than 0.5, greater than 0.5 and less than 3, greater than 0.5 and less than 2.5, greater than 0.5 and less than 2.0, greater than 0.5 and less than 1.5, greater than 0.5 and less than 1.0, greater than 1 and less than 3, greater than 1 and less than 2.5, greater than 1 and less than 2.0, greater than 1 and less than 1.5, greater than 1.5 and less than 3, greater than 1.5 and less than 2.5, greater than 1.5 and less than 2.0, greater than 2 and less than 3, greater than 2 and less than 2.5, and greater than 2.5 and less than 3.

Figure 7B:
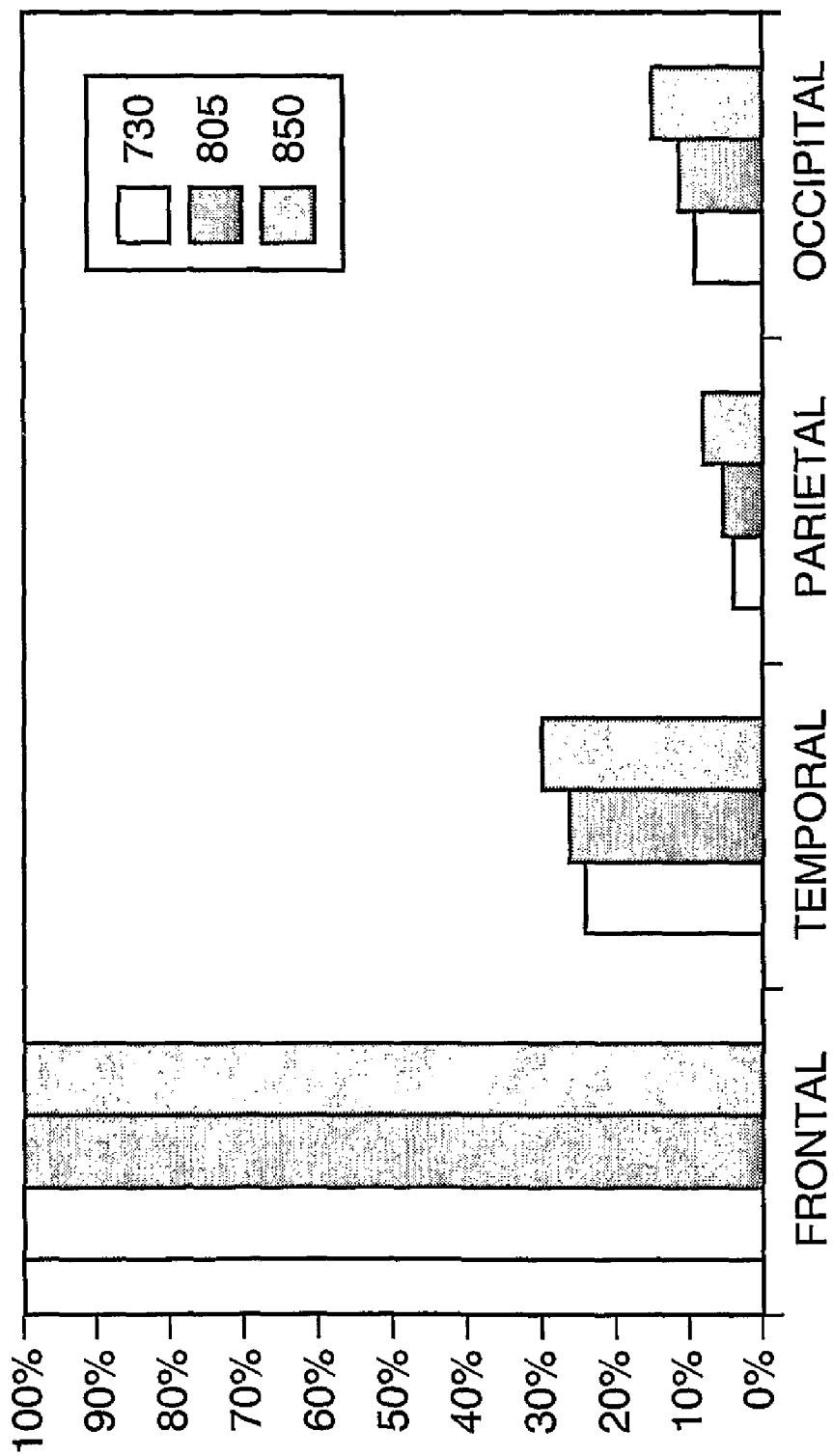
FIGS. 7B-7D illustrate data resulting from a detection method of an embodiment of the present invention.
Figure 7C:
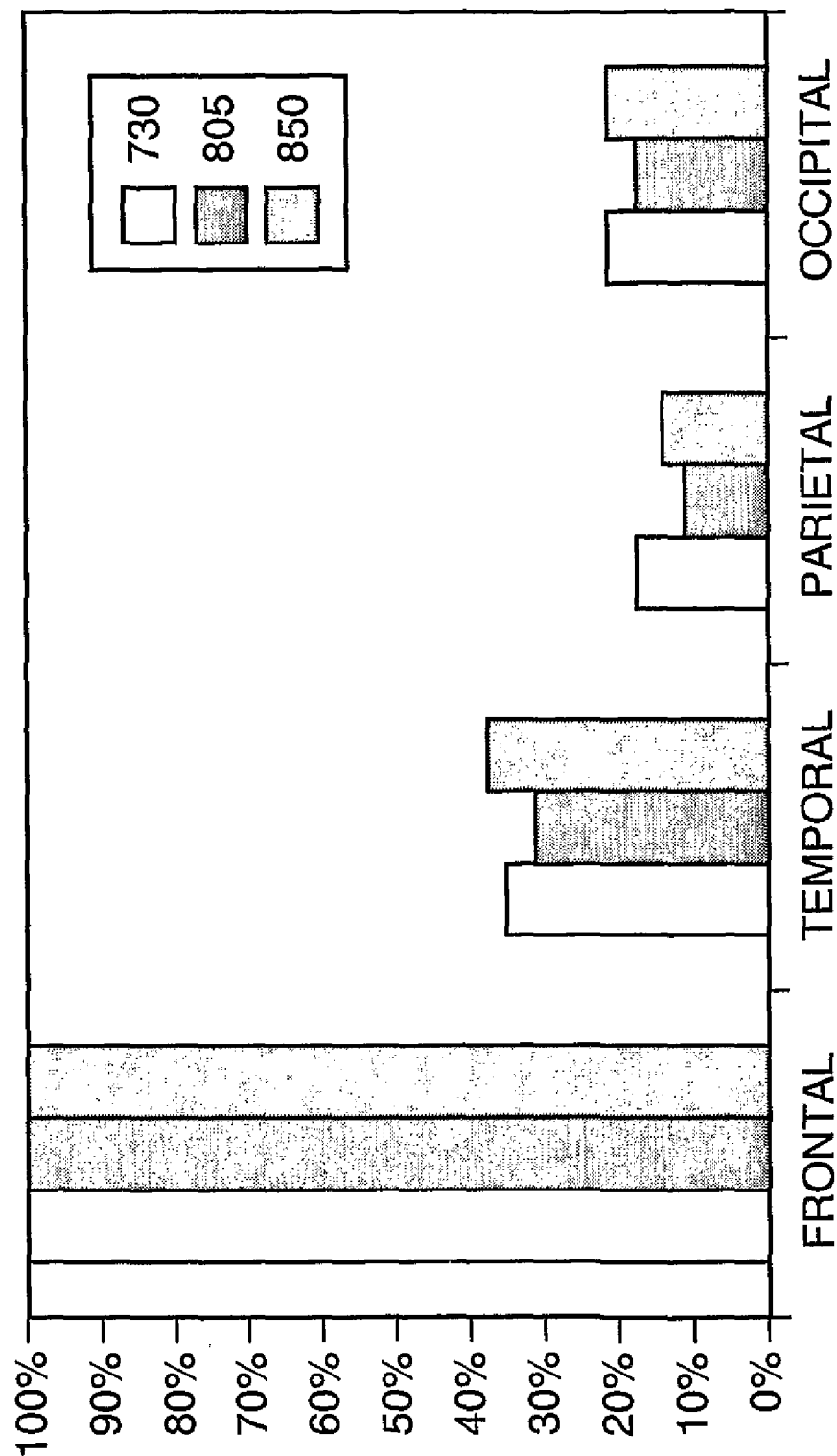
Figure 7D:
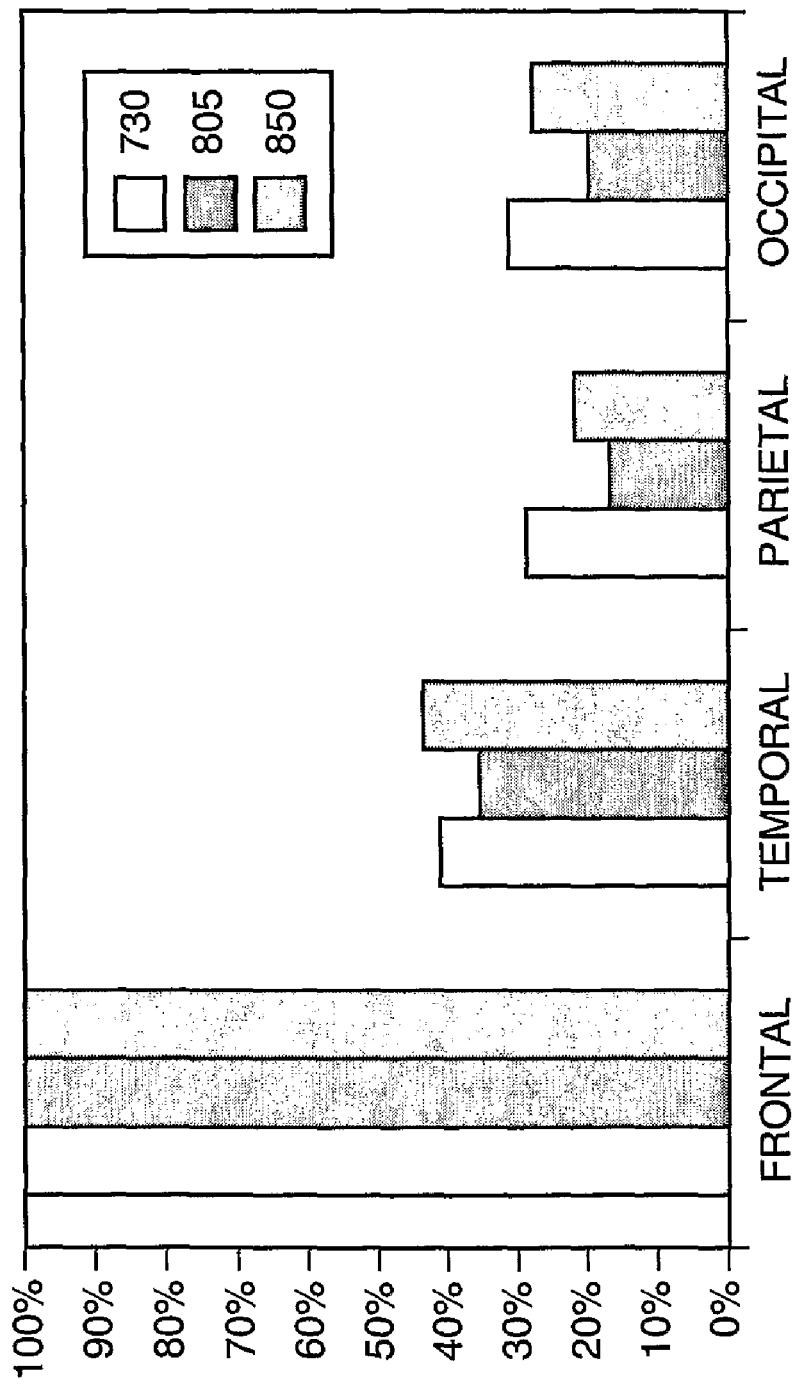

In a preferred method of detecting bilateral hematoma, there is a predictable degree of attenuation of light as between the four lobes on one side of the head. In one embodiment, that predicable degree is attributable, for example, to typically thicker skull bone or and/or hair follicles in certain head locations. In one embodiment, hair follicles and thicker bone will reduce signal by approximately 80% in the top and back of the head, as compared to the forehead, for example. In one embodiment, this causes frontal measurements to indicate less attenuation than temporal measurements which indicate more attenuation than occipital measurement which indicate more attenuation than parietal measurements. In one embodiment, for each side of a normal patient's head, the optical density value of the normal patient's temporal lobe is approximately 35% of the optical density value of the normal patient's frontal lobe; the optical density value of a normal patient's parietal lobe is approximately 18% of the optical density value of the normal patient's frontal lobe; and the optical density value of a normal patient's occipital lobe is approximately 20% of the optical density value of the normal patient's frontal lobe. FIGS. 7B, 7C and 7D indicate normalized values of signal strength for each of a frontal lobe, temporal lobe, parietal lobe and occipital lobe as determined by system 100 with the distance between detector 127 and light source 121 of 2 cm (FIG. 7B), 3 cm (FIG. 7C) and 4 cm (FIG. 7D). The data in FIGS. 7B-7D illustrate signal strength at a wavelength of light source 121 of 730 nm, 805 nm and 850 nm. FIGS. 7B-7D illustrates that the signal strength for each detector and light source configuration tested decreases in the order of frontal, temporal, occipital and parietal. In each of FIGS. 7B to 7D, the signal strength for the frontal lobe is shown to be unity with each of the temporal, occipital and parietal lobes shown as a percentage of frontal lobe signal strength.

Figure 8A:
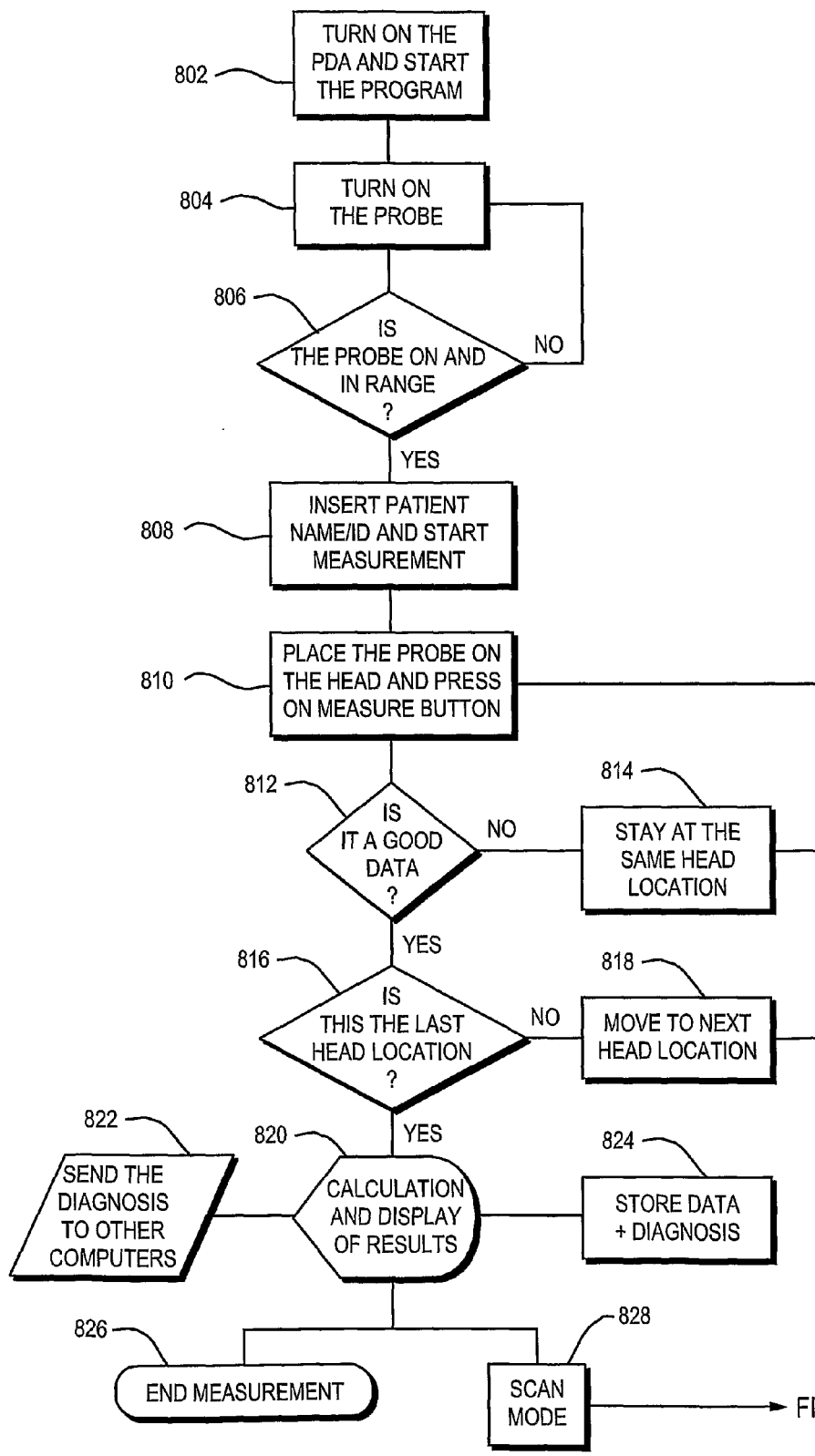
FIGS. 8A-8B illustrate an embodiment of a method of brain hematoma detection of the present invention.
Figure 8B:
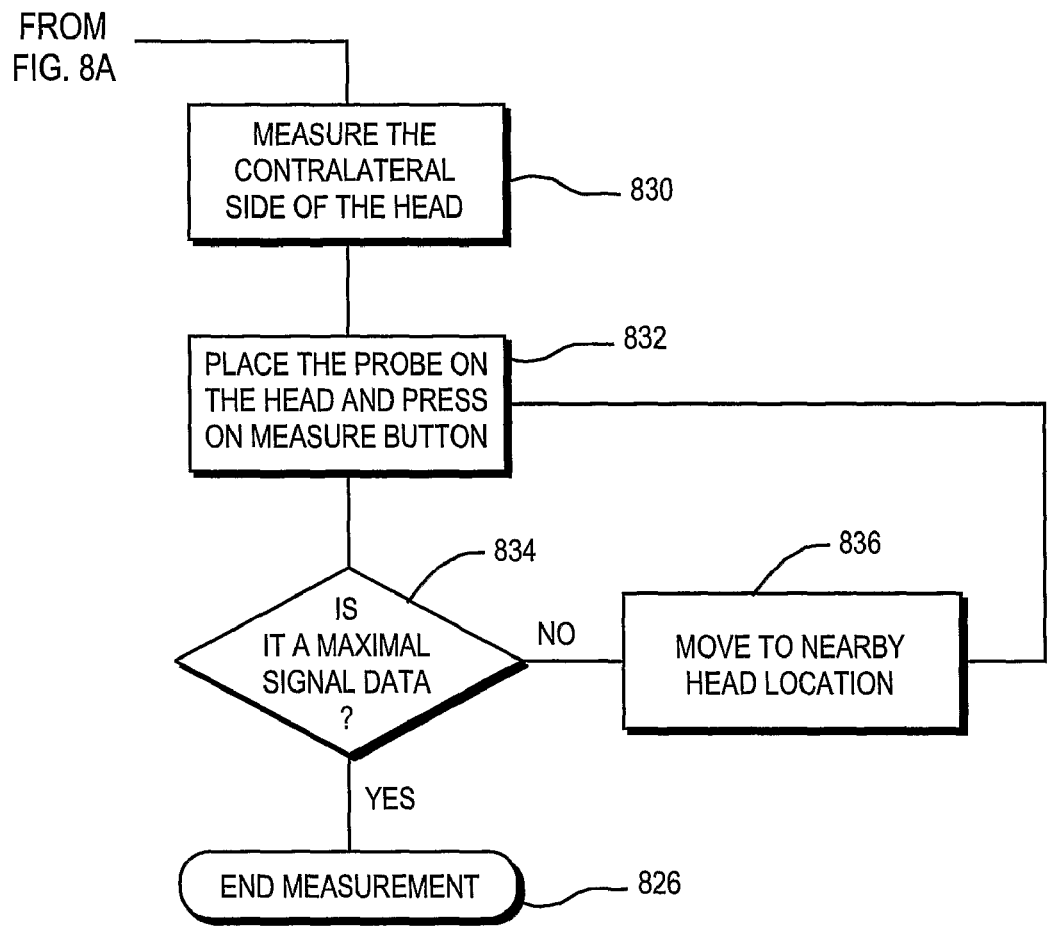
Figure 9A:
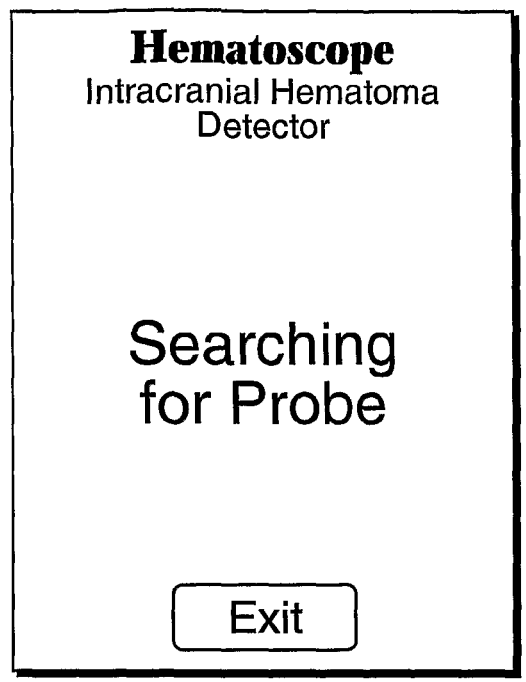
FIGS. 9A-9G illustrate exemplary screen shots of a system of the present invention.
Figure 9B:
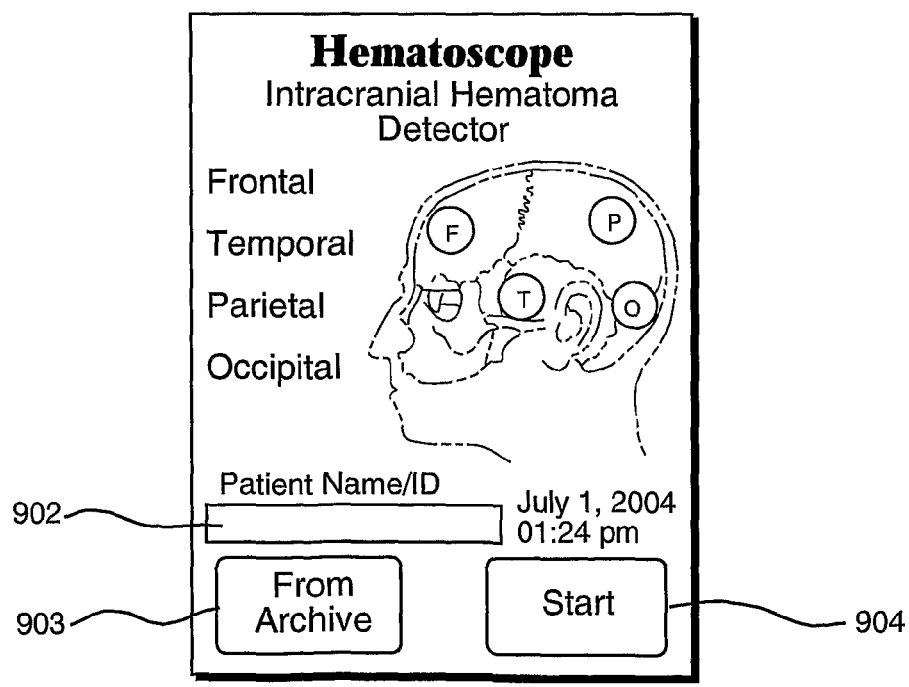

FIGS. 8A-8B illustrate an embodiment of the operation of system 100. In step 802 of FIG. 8A, processor 140 (e.g., a computing system such as a personal digital assistant) is powered and booted. In step 804 of FIG. 8A, probe 120 is powered after processor 140 is running. In step 806, processor 140 searches for probe 120 which in the embodiment of FIGS. 8A-8B are connected, for example, by a wireless link as described above. In one embodiment, processor 140 (e.g., Bluetooth® enabled processor) is preferably configured to identify all compatible transmitters (e.g., Bluetooth® enabled transmitters) within a given range; including, for example, each probe 120 within range. If probe 120 is not within range, processor 140 will continue to search until probe 120 is brought within range or a preset number of loops is reached (i.e., the device times-out). In one embodiment of the present invention, FIG. 9A illustrates a screen display indicating that processor 140 is searching for probe 140 (e.g., during step 806). If probe 120 is in range, a user of one embodiment of system 100 is prompted to insert patient data (e.g., name, ID, other identifying information) at step 808. As illustrated, for example, in FIG. 9B, an operator (e.g., a care giver such as a paramedic, nurse or physician) of system 100 then has the option to enter new patient information in field 902 or select a patient from an archive of patients stored in a memory (e.g., a memory resident in processor 140, external to processor 140 and/or linked to processor 140), by selecting link 903. After entering the patient data or selected data from storage, the user starts the measurement process by pressing start 904.

Referring again to FIGS. 8A-8B, at step 810, the user begins measurement by placing probe 120 on the patient's head at a desired location illustrated, for example, in FIGS. 1A and 1B. The desired location is determined, in one embodiment, by selecting one of a pre-selected number of routines (e.g., one of the routines illustrated in FIGS. 5A-5D). After placing the probe in the desired head location, the user in one embodiment initiates the measurement using probe 120 (e.g., by depressing and releasing measurement switch 250 (FIG. 2C)). In one embodiment, measurement switch 250 remains engaged until the user hears an audible alert indicate the measure was successfully taken. In another embodiment, measurement switch 250 is pressed and released prior to hearing the audible alert. In another embodiment, multiple audible alerts are available to distinguish, for example, successful measurements and unsuccessful measurements.

In an embodiment of system 100, upon initiation of the measurement routine, probe 120 signals processor 140 that it is ready to begin measurement. Thereafter, processor 140 initiates a data acquisition sequence. The data acquisition sequence, of one embodiment, will continue until valid data has been collected or the user terminates the measurement. Processor 140 preferably performs substantially all of the data processing and parameter selection for system 100.

Probe 120, in one embodiment, performs according to commands provided by processor 140. In another embodiment, all data collection, storage and measurement commands are performed within probe 120. In one embodiment, processor 140 displays and stores data as commanded by probe 120. In one embodiment, processor 140 sends a Do Measurement command to probe 120 after processor 140 and probe 120 hand shake. In one embodiment, illustrated in FIG. 13, the Do Measurement command sets necessary data acquisition parameters of probe 120 and probe 120 performs the data acquisition. In one embodiment, after the Do Measurement command is issued, probe 120 sends a Measurement Data command containing the collected data to processor 140. In one embodiment, the Do Measurement command sets all or less than all of laser power, number of laser pulses, period of laser pulses, pulse width and gain. In one embodiment, the Do Measurement command also commands probe 120 on the type of data process (e.g., according to averages, direct measurement, etc.).

In the embodiment of FIG. 13, if the Average parameter is set to 1, an average is used. Also in the embodiment of FIG. 13, the Laser Power parameter takes values between 0 mW and 100 mW. In one embodiment, the Laser Power parameter is transmitted with 1 byte and it is the first byte in the command body.

In the embodiment of FIG. 13, Number of Pulses parameter takes values between 0 and 1000. It is transmitted with 1 byte and it is the second byte in the command body. Also in the embodiment of FIG. 13, Period Of Laser Pulses is approximately 300 milliseconds and has a range between 100 to 1000 milliseconds. In one embodiment, the period is meaningful only in quanta of 10 milliseconds. In one embodiment the value of Period Of Laser Pulses is transmitted as $\frac{1}{10}$ of the original. For example, to set 300 milliseconds, '30' is transmitted. By transmitting $\frac{1}{10}$ of the original value, data is kept in single byte limits. In one embodiment, Period Of Laser Pulses is transmitted with 1 byte and it is the third byte in the command body.

FIG. 13 also illustrates the Pulse Width parameter. In one embodiment, Pulse Width is approximately 4 milliseconds and is the range of between 1 and 10 milliseconds. In one embodiment, Pulse Width is transmitted with 1 byte and it is the fourth byte in the command body.

FIG. 13 further illustrates Gain parameter which takes values between 0 and 255. In one embodiment, Gain parameter is transmitted with 1 byte and it is the fifth byte in the command body. The parameters are either default staring parameters (e.g., to start the calibration) or the parameters from the calibration.

In one embodiment, each command of processor 140 includes light source power (e.g., laser power), detector gain settings and the number of pulses that probe 120 is to perform for the given parameters. In one embodiment, probe 120 signals processor 140 that measurement is enabled and processor 140 returns to probe 120 default parameters (e.g., laser power=50; detector gain=50; and number of pulses=3) for system 100. In one embodiment, probe 120 conducts the measurement by initiating a pulse. In one embodiment, each pulse includes a light pulse from light source 121 for 10 milliseconds (ms), a rest of 40 ms, 10 ms of dark current and then another 40 ms of rest. In one embodiment, this produces an effective rate of 10 measurements per second. In another embodiment, rest periods are increased beyond 40 ms and peak power of light source 121 is increased. The higher peak power is facilitated by a longer rest and therefore a longer "cool-down" period.

In one embodiment, probe 120 reports collected data to processor 140. Then, based upon the data collected, processor 140 determines parameters for the next command. For example, the next command could be to increase or decrease power, or increase or decrease gain).

Figure 9C:
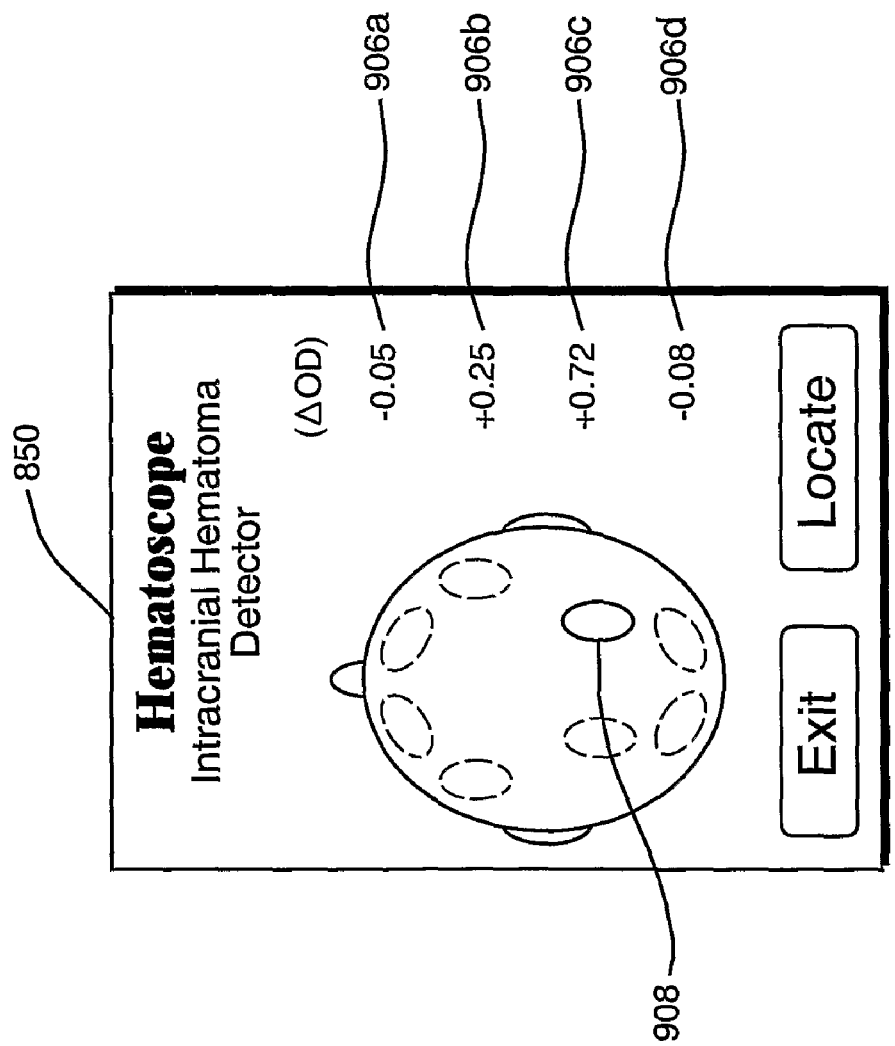

Referring again to FIGS. 8A-8B, in step 812, in one embodiment, processor 140 performs an evaluation of whether the data collected (e.g., returned from probe 120) is valid data (described in more detail below). In one embodiment, if the collected data is valid and no additional head locations remain to be tested, calculated values and graphic display results are presented to the user at step 820. In one embodiment, data values are averaged for purposes of evaluating the validity of data. Also in one embodiment, the average value is presented to the user at step 820. One embodiment of a results display is illustrated in FIG. 9C. FIG. 9C is a screen shot reporting calculated values 906a-906d as: Frontal $\Delta OD$=–0.05 (906a), Temporal $\Delta OD$=+0.25 (906b); Occipital $\Delta OD$=+0.72 (906c); and Parietal $\Delta OD$=–0.08 (906d). In one embodiment, value of Occipital $\Delta OD$ of +0.72 exceeds the predetermined limit, for example, of 0.3 and therefore indicates occipital hematoma. Because the value of occipital $\Delta OD$ is positive, in this embodiment, the occipital hematoma is determined to be right occipital hematoma and graphical indicator 908 is displayed accordingly.

Returning to FIG. 8A, in one embodiment, after the calculated results and graphics are displayed (e.g., as in FIG. 9C), the diagnosis data is stored in step 824 and/or sent to other users in step 822.

Figure 8C:
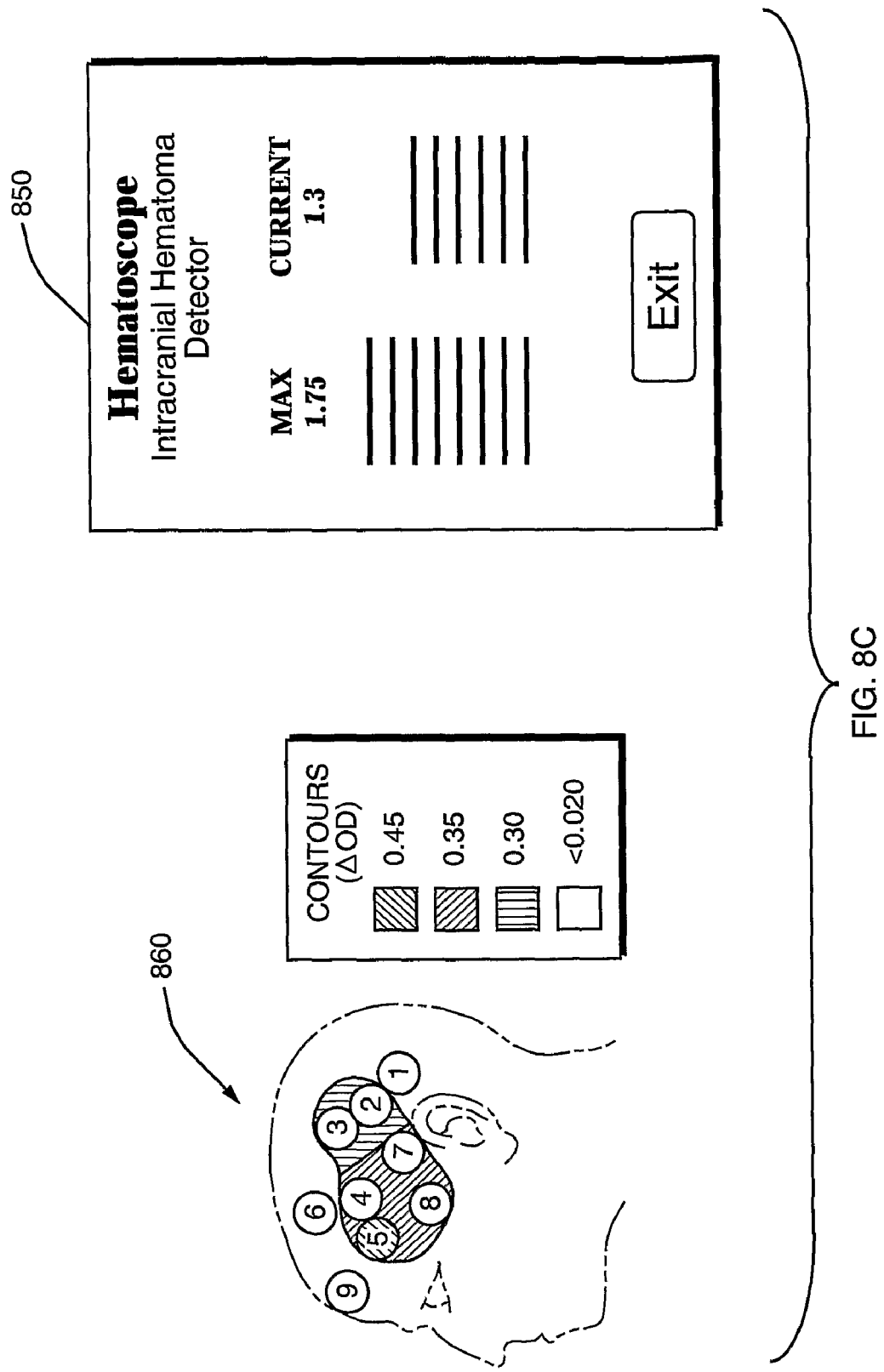
FIG. 8C illustrates an exemplary display of the device of an embodiment of the present invention.

In one embodiment, such as a battlefield or other trauma setting with limited resources, it might be desirable to more specifically locate the hematoma so, for example, treatment such as draining the hematoma can begin immediately in the field upon diagnosis. In one embodiment, illustrated in FIG. 8C, it is desirable to create a contour profile of the hematoma to more precisely locate the hematoma within a particular lobe. In one embodiment, a more precise location of hematoma begins at step 830 of FIG. 8B. Should one determine that unilateral hematoma exists in the left temporal lobe, for example, a user first measures the optical density at the contralateral location (in this example, the right temporal lobe). Then in step 832, for example, the user places probe 120 on a desired head where hematoma has been diagnosed such as by the methods described herein (in this example, the user places probe 120 on one location corresponding to the left temporal lobe) and initiates the optical density measurement such as described herein. The optical density is recorded and optionally displayed in screen shot 850. The user may then move probe 120 to a nearby location (step 836) still corresponding to the region of interest (e.g., the left temporal lobe) and take another optical density measurement. In one embodiment, that nearby location is preselected. In another location that nearby location is selected by the user in the field. In this fashion, the user may create a contour map illustrating the optical densities throughout a particular region of the brain (e.g., the left temporal lobe). In one embodiment, the user is presented with a graphical display in real time such that the user can immediately evaluate whether the probe is being moved toward or away from the hematoma site. In one embodiment, illustrated in FIG. 8C, the graphical contour map 860 is displayed for the user and/or field technician. For example, contour map 860 shows regions of varying optical density along with a graphical display of the optical density in the corresponding region. In one embodiment, both a tabular (e.g., table 850) and graphical representation 860 are displayed for the user. In one embodiment, at step 834 multiple data is compared to identify whether the maximal optical density has been achieved whereupon treatment of the hematoma may be initiated. In another embodiment, table 850 displays the current measurement and the maximum measurement to facilitate diagnosis by the user. In one embodiment, software in processor 140 graphically interprets optical density measurements to create contour map 860 which also identifies the specific location of the hematoma. In one embodiment, processor 140 is configured to display both the presence of brain hematoma and the local oxygen saturation in the measured sites.

Returning to step 816 of FIG. 8A if data remains to be collected for the patient being tested, processor 140 instructs probe 120 to expect data for the next measurement location in step 818. If the collected data is not valid, processor 140 instructs probe 120 to re-measure at the same head locations as in step 814.

Figure 10:
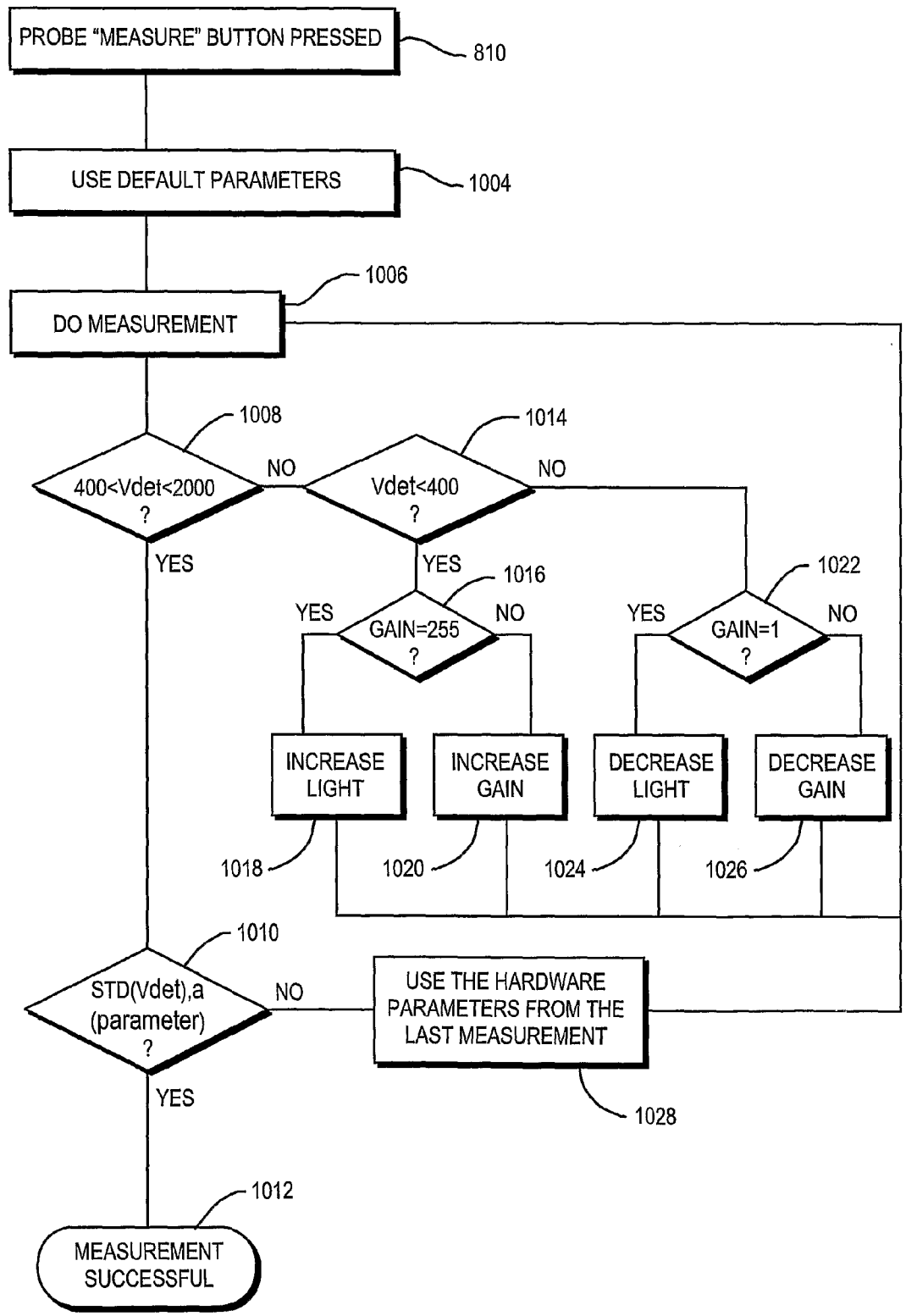
FIG. 10 illustrates one embodiment of a method of calibrating a system of the present invention.

FIG. 10 illustrates one embodiment of a measurement algorithm to determine data validity (e.g., at step 812 of FIG. 8A). Upon engagement of the measurement switch (step 810 in FIG. 10), default parameters are returned to probe 120 in step 1004. Probe 120 then performs the measurement in step 1006. In one embodiment, measurement data is then returned to processor 140. In one embodiment, the measurement data in step 1006 includes the detector voltage. In one embodiment, the measurement data in step 1006 is only the detector voltage because of the other parameters were collected prior to the measurement step. If, as is illustrated in step 1008, detector voltages is between two selected parameters (e.g., 400 mV and 2000 mV) the standard deviation of the detector voltage is determined in step 1010. If, in step 1010, the standard deviation of the detector voltages is below an acceptable value the measurement data is determined to be valid. In one embodiment, the acceptable value of standard deviations is approximately 15%. If however, the detector voltage in steps 1008 and 1014 is below the predetermined range (e.g., below 400 mV) and at a certain gain (e.g., 255) then processor 140 instructs probe 120 to increase the power of light source 121 (step 1018). In one embodiment, the increase in power is by a factor (e.g., 3, 5 or 10) and the measurement is run again. In one embodiment the factor is fixed such that each power increase is made by the same factor. If the gain in step 1016 is not 255 then gain is increased by, for example, a fixed factor and the measurement is performed again.

If the measurement data indicates that detector voltage, in steps 1008 and 1014, is greater than the predetermined range (e.g., greater than 2000 mV) at a certain gain (e.g., equal to 1), processor 140 instructs probe 120 to decrease light source power and run the measurement again. In the embodiment of FIG. 10, when the measurement data indicates that detector voltage, in steps 1008 and 1014, is greater than the predetermined range and at a certain gain (e.g., not equal to 1), processor 140 instructs probe 120 to decrease detector gain and run the measurement again. This process of automatic calibration preferably continues until a valid measurement is returned or the process "times-out." In one embodiment, the process "times-out" when a preset number of automatic calibration loops is performed.

In one embodiment, therefore, there is a method of detecting hematoma without repeating calibrations that includes, based upon predetermined parameters, calculating a signal intensity associated with each head location in at least one pair of contralateral head locations; and determining a difference in optical density for the at least one pair of contralateral head locations based upon the calculated signal intensity; and indicating the possibility of hematoma based upon the comparison of the difference in optical density for the at least one pair of contralateral head locations with a predetermined range.

Calibration. In one embodiment, system 100 is calibrated prior to each measurement event (e.g., for each measurement location). In one embodiment, the purpose of calibration is to optimize system parameters (e.g., maximize dynamic range) to ensure that the signal received from detector 127 is in an acceptable sampling range. During a calibration step of one embodiment, system parameters are changed based upon maximizing signal to noise ratio (S/N). Maximizing S/N may include, for example, maximizing power of light source 121 and minimizing gain of detector 127. For example, in one embodiment, if a signal at detector 127 is too weak, system 100 will increase light intensity. In one embodiment, the increase in light intensity will be to the maximum light intensity of light source 121. If the signal is still too weak, in one embodiment, system 100 will increase gain of detector 127 on an iterative basis until the signal is in an acceptable range. Alternatively, in one embodiment, if the signal is too weak, gain will be increased first followed by an iterative increase in light intensity from light source 121 to bring the signal into an acceptable range.

For one embodiment, each new measurement sequence begins with system default settings. In another embodiment, for each successful measurement, system 100 associates the successful measurement with the corresponding parameters setting and head location thereby enabling that parameter setting to be used for the contralateral head location. In one embodiment, therefore, contralateral measurement sequences begin with the parameters setting from a successful measurement of the patients' contralateral tissue rather than with a default setting but. For example, the parameters used to successfully measure OD from a patient's left temporal lobe will be used to measure OD of the patient's right temporal lobe.

In one embodiment, calibration starts with the assumption that system 100 is linear. In one embodiment, for example, it is assumed that there is a linear relationship between the power of light source 121, gain of detector 127 and the measured signal. In one embodiment, illustrated in FIG. 11 calibration tables (e.g., tables 1102 and 1104) are maintained for system 100. In one embodiment, separate calibration tables are maintained for each probe in system 100. In FIG. 11, calibration tables 1102 and 1104 correlate measured values with the power of light source 121 (e.g., laser power) and with detector gain respectively. In one embodiment, the relationship between measured value and system parameters as stored in calibration tables 1102 and 1104 mitigate errors associated with a presumed linearity by more precisely predicting system non-linearity. In one embodiment, the maximum number of entries in tables 1102 and 1104 is 20. In one embodiment, tables 1102 and 1104 are normalized to normalize light source power and gain respectively. Measurements taken by system 100 may thereafter be corrected for the system non-linearity as reflected, for example, in tables 1102 and 1104 to more precisely determine optical density.

In one embodiment, tables 1102 and 1104 are used to evaluate system 100 hardware. For example, in one embodiment, if a measured value represents a dramatic departure from the value predicted by tables 1102 and/or table 1104, there is an indication that system 100 requires maintenance. Maintenance, in one embodiment, includes disposal and replacement of light guide assembly 200, light source 121 and/or detector 127.

Figure 9D:
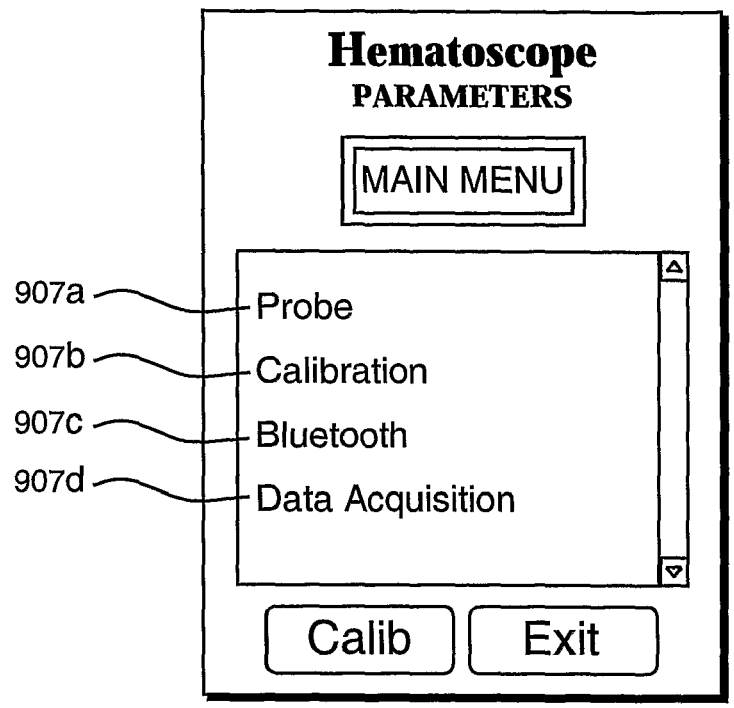
Figure 9E:
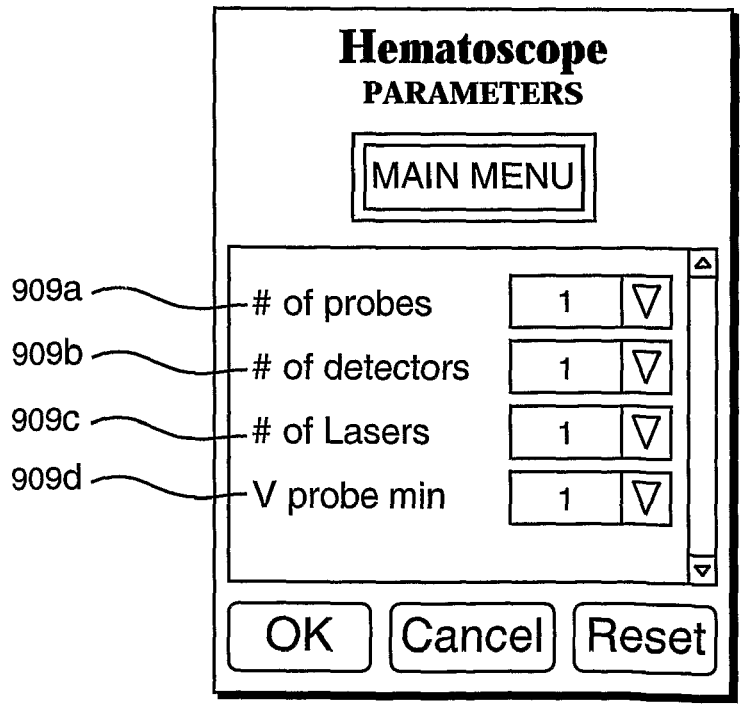
Figure 12:
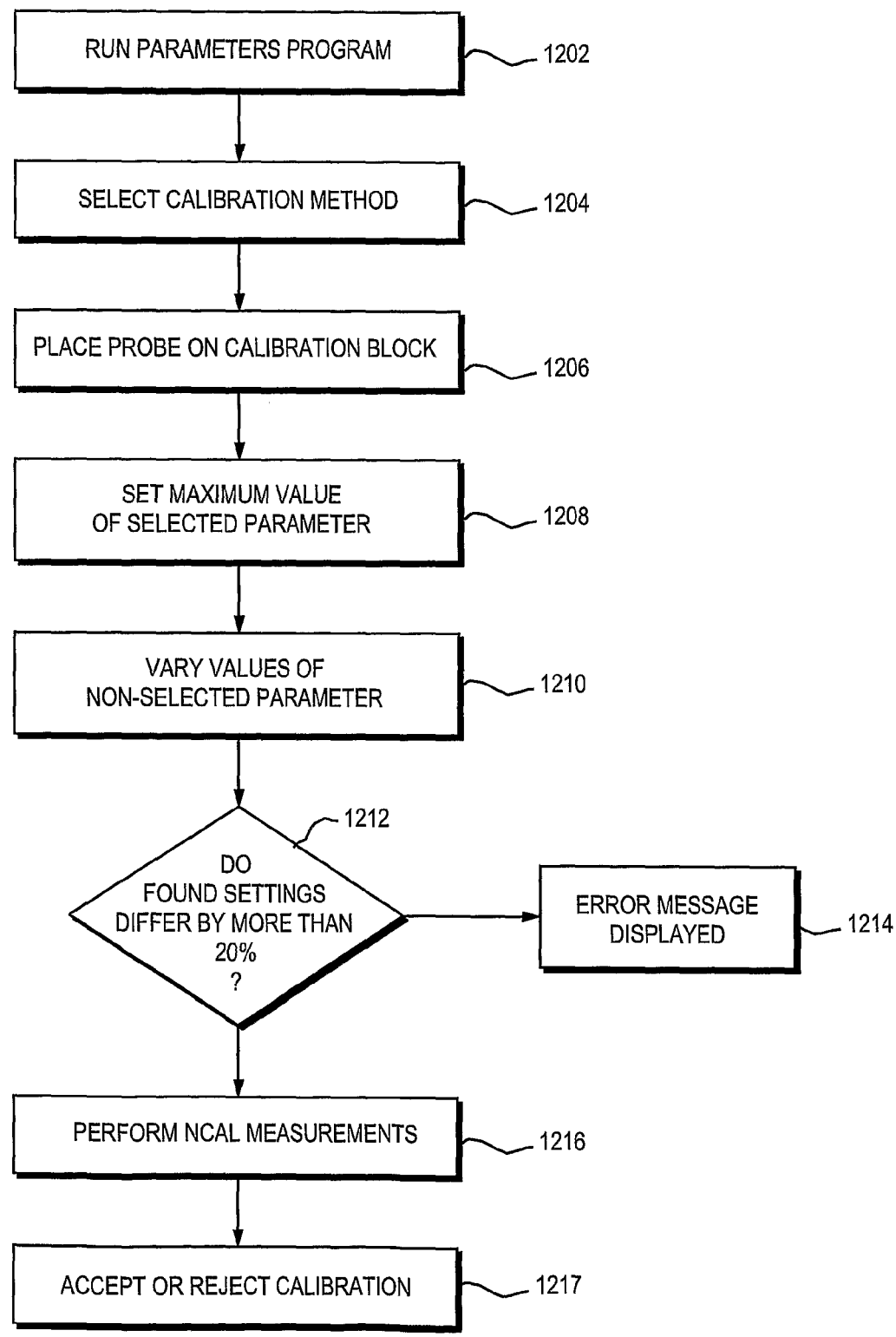
FIG. 12 illustrates one embodiment of a calibration method for use in one embodiment of the present invention.

FIG. 12 illustrates one embodiment of a calibration sequence. In step 1202 a user of system 100 is prompted to run a parameters program. In one embodiment, the calibration sequence is run on a routine periodic basis (e.g., each week or month). In one embodiment, a screen shot for which is illustrated in FIG. 9D, the parameters program includes options to set probe parameters, to calibrate system 100, to set for example, Bluetooth® parameters, and to set data acquisition parameters. In the embodiment depicted in FIG. 9D a parameters program option is picked by selecting (e.g., tapping with a stylus or a finger, or navigating with a click wheel or any other selecting mechanism) one of the buttons 907a-907d. For example, if a user selects the probe button 907a of the parameters menu illustrated in FIG. 9D, the user is redirected to a screen, illustrated in FIG. 9E where a number of probe parameters may be specified. In the embodiment of FIG. 9E those parameters include all or some of the number of probes in use 909a, the number of detectors in use 909b, the number of lasers in use 909c, and minimum probe voltage 909d.

Figure 9F:
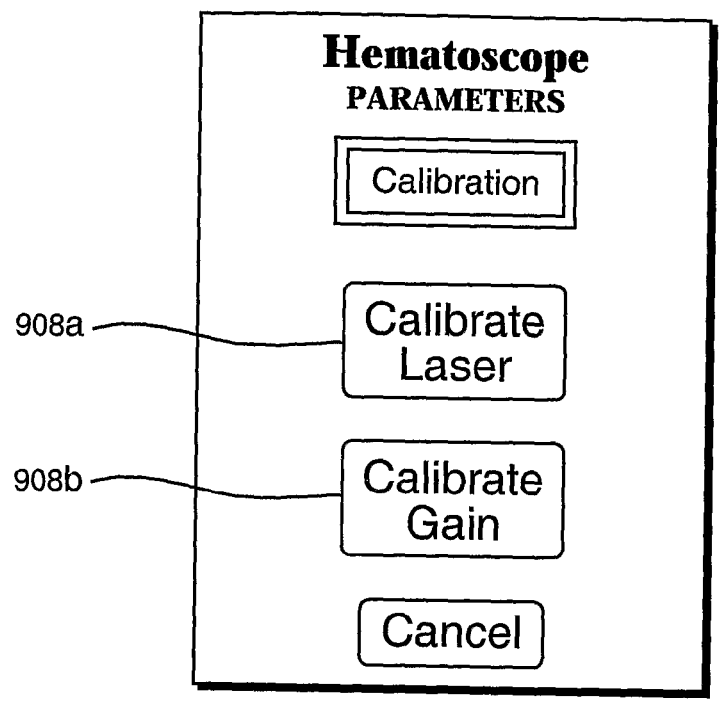

In step 1204 (FIG. 12), a user of system 100 selects the calibration mode 907b (FIG. 9D). In one embodiment, the user is prompted to place probe 120 on a calibration block and activate the calibration sequence. The calibration block, in one embodiment, has a known OD. In one embodiment the known OD approximates the OD of typical human tissue. In one embodiment optical density is a function of a parameter of absorption $\mu_a$ and a parameter of scattering $\mu_s$. In one embodiment, the optical density of a calibration block having an optical density approximating that of human tissues is characterized by $\mu_a$=0.12 and $\mu_s$=10. In one embodiment, a display on processor 140 will indicate the calibration in progress status of system 100. The user, in one embodiment illustrated in FIG. 9F, is prompted to select the parameter for calibration (e.g., laser power 908a or gain 908b). A user may also cancel the calibration step at any time.

Returning to FIG. 12, system 100, in step 1208, sets the maximum value of the calibration parameter selected (e.g., selected by the user as described above, or automatically by processor 140). In step 1210, the non-selected parameters are varied. For example, in the calibration of light source 121 (e.g., laser calibration), gain will be varied and, in gain calibration, light source power will be varied. In one embodiment, probe 120 takes iterative readings for each combination of light source power and detector gain until detector signal reaches a pre-selected level (e.g., 4000 mV). In one embodiment, the setting corresponding to the pre-selected level (e.g., 4000 mV) is maintained throughout the calibration process. In one embodiment, if the setting corresponding to the pre-selected level varies by more than a fixed percent (e.g., 20%) from the setting of a previous calibration process (e.g., the immediately preceding calibration) an error message is displayed. In one embodiment, the error message is an indication of a hardware defect such as weak light source 121, faulty detector 127, or a defect in one or more light guides 128. In one embodiment, after the calibration setting is determined and found to be within an acceptable percent of previous calibrations, system 100 will perform a pre-selected number (given the variable designation Ncal, for example) of successive measurements (step 1216) for each point in the calibration table (e.g., table 1102 and 1104 illustrated in FIG. 11) and populate the calibration table with an average of the Ncal measurements. In one embodiment Ncal is in the range of 1 to 10. In one embodiment, the number of pulses during calibration is set at 3 (e.g., Ncal=3) and the number of pulse during active measurement is set at 10 (e.g., Ncal=10).

Figure 9G:
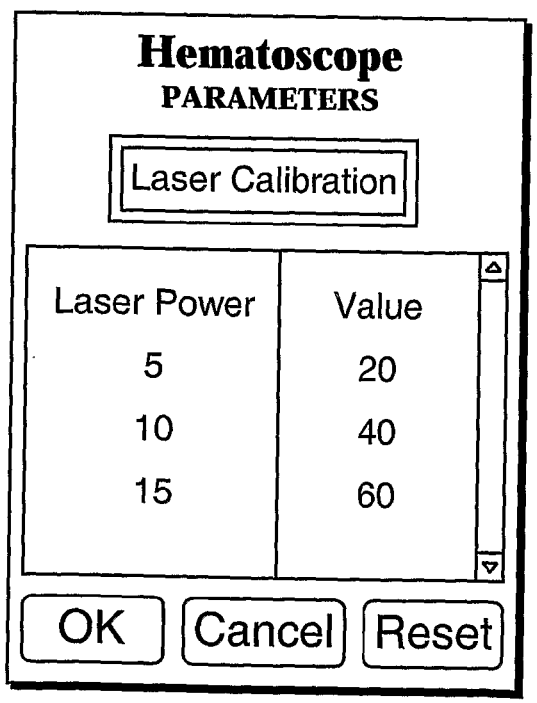

Once the calibration table is populated the calibration measurement step is terminated. In one embodiment, such as illustrated in FIG. 9G, once data collection has been finished, the results are presented in tabular form to the user of system 100 who may either accept or reject the calibration (step 1217). In one embodiment, acceptance of the current calibration table will cause the current calibration table to replace the previously saved calibration table in system 100. In one embodiment, a user will have the option to use a default calibration table.

Although the foregoing description is directed to the preferred embodiments of the invention, it is noted that other, variations and modifications in the details, materials, steps and arrangement of parts, which have been herein described and illustrated in order to explain the nature of the preferred embodiment of the invention, will be apparent to those skilled in the art, and may be made without departing from the spirit or scope of the invention.

This application claims priority to U.S. Provisional Patent Application No. 60/678,519 filed May 6, 2005 and U.S. Provisional Patent Application No. 60/787,383 filed Mar. 30, 2006 each of which is incorporated by reference as if set forth in their entirety herewith. All references cited herein are incorporated by reference as if set forth in their entirety herewith.

The invention claimed is:

1. A system for indicating a bilateral hematoma condition comprising:
   memory storing at least one program; and
   at least one processor communicatively coupled to the memory in which the at least one program when executed by the at least one processor, causes the at least one processor to:
      determine an optical density associated with a plurality of brain locations on a right side of a patient's head;
      determine a first optical density difference between two of the plurality of brain locations on the right side of the patient's head;
      determine an optical density associated with a plurality of brain locations on a left side of the patient's head;
      determine a second optical density difference between two of the plurality of brain locations on the left side of the patient's head; and
      indicate bilateral hematoma based upon a comparison of the first optical density difference and the second optical density difference to a predetermined optical density difference range.

2. A system of indicating a hematoma condition comprising:
   memory storing at least one program;
   at least one processor communicatively coupled to the memory in which the at least one program, when executed by the at least one processor, causes the at least one processor to:
      determine an optical density difference for at least one pair of contralateral head locations;
      compare said optical density difference to a predetermined range of optical density differences; and
      diagnose a hematoma condition in each of the contralateral head locations based upon a relationship between the optical density differences and the predetermined range of optical density differences and
   a hand held probe having a base with at least one radiation detector, at least one light source and a removable light guide assembly having at least one detector light guide configured to align with the radiation detector and at least one source light guide configured to align with the light source, the light guide assembly being removably secured to the base.

3. A system for detection of a hematoma comprising:
   a handheld probe having:
      a base including:
         a source of infrared light, and
         a detector of infrared light, and
         a light guide assembly secured to the base and including:
            a source light guide that transmits infrared light from the source to a tissue region, and
            a detector light guide that transmits at least a portion of the infrared light passing through the tissue region to the detector; and
      a processor linked to the probe, configured to provide instructions to the probe and configured to process data transmitted by the probe, the processor having a display configured to indicate the presence of a hematoma based upon a characteristic of the infrared light passing through the tissue region.

4. The system of claim 3 wherein the probe and processor are housed in the base.

5. The system of claim 3 wherein the probe and the processor are linked with a wireless link.

6. The system of claim 3 wherein the base is contiguous with the source light guide and the detector light guide, and the light guide assembly is removeably secured to the base.

7. The system of claim 3 wherein the source light guide and the detector light guide are moveably attached to a cover of the light guide assembly, the source light guide and the detector light guide being spring biased relative to the cover in a direction away from the base.

8. The system of claim 7 wherein the source light guide and the detector light guide are independently moveable with respect to one another.

9. The system of claim 3 wherein the light guide assembly includes an opaque cover radially disposed around each of the source light guide and the detector light guide.

10. The system of claim 3 wherein the base includes a plurality of detectors of infrared light and the light guide assembly includes a plurality of detector light guides that each transmit at least a portion of the infrared light passing through the tissue region to one of the plurality of detectors.

11. A hand held device for use in detecting a hematoma comprising:
    a base having:
       at least one radiation detector, and
       at least one light source; and
    a light guide assembly removeably secured to the base by at least one of a friction fit between the base and the light guide assembly, a sealed securement between the base and the light guide assembly or one or more fasteners, the light guide assembly having:
       at least one detector light guide configured to align with the radiation detector, and
       at least one source light guide configured to align with the light source.

12. The hand held hematoma detection device of claim 11 wherein the light guide assembly further comprises at least one external support.

13. The hand held hematoma detection device of claim 11 wherein at least one of the detector light guides and the source light guides are configured to resiliently depress relative to the base.

14. The hand held hematoma detection device of claim 11 wherein the detector light guide and the source light guide protrude from a distal end of the light guide assembly and the light guide assembly further comprises a lip at the proximal end of the light guide assembly.

15. The hand held hematoma detection device of claim 11 wherein the light guide assembly includes a cover having:
 a contiguous lip,
 contiguous cladding radially disposed about the detector light guide,
 contiguous cladding radially disposed about the source light guide,
 a contiguous light dam associated with the light source, and
 a contiguous light dam associated with the detector.

* * * * *